United States Patent
Watanabe et al.

(10) Patent No.: US 12,366,565 B2
(45) Date of Patent: *Jul. 22, 2025

(54) GAS SENSOR AND METHOD OF DIAGNOSING MOISTURE ABSORPTION STATE OF GAS SENSOR

(71) Applicant: NGK INSULATORS, LTD., Aichi (JP)

(72) Inventors: Yusuke Watanabe, Nagoya (JP); Ryo Hashikawa, Nagoya (JP); Daichi Ichikawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 283 days.

This patent is subject to a terminal disclaimer.

(21) Appl. No.: 18/079,026

(22) Filed: Dec. 12, 2022

(65) Prior Publication Data

US 2023/0194493 A1    Jun. 22, 2023

(30) Foreign Application Priority Data

Dec. 16, 2021 (JP) .................................. 2021-203831
Nov. 30, 2022 (JP) .................................. 2022-191635

(51) Int. Cl.
*G01N 27/407* (2006.01)
*G01N 33/00* (2006.01)

(52) U.S. Cl.
CPC ..... *G01N 33/0037* (2013.01); *G01N 27/4074* (2013.01); *G01N 27/4076* (2013.01)

(58) Field of Classification Search
CPC .......... G01N 33/0037; G01N 27/4074; G01N 27/4076; G01N 27/4175; G01N 27/419;
(Continued)

(56) References Cited

U.S. PATENT DOCUMENTS

2020/0191744 A1    6/2020    Watanabe

FOREIGN PATENT DOCUMENTS

CN         113447554 A   *  9/2021    .......... G01M 15/102
JP         2020-094899 A     6/2020

OTHER PUBLICATIONS

Unexamined U.S. Appl. No. 18/079,025, filed Dec. 12, 2022.

* cited by examiner

*Primary Examiner* — Robert R Raevis
(74) *Attorney, Agent, or Firm* — Mattingly & Malur, PC

(57) ABSTRACT

A gas sensor includes a sensor element and a controller. The sensor element includes an element body provided with a measurement-object gas flow section therein, a measurement electrode disposed in the measurement-object gas flow section, an outer pump electrode provided in the element body so that the outer pump electrode comes into contact with a measurement-object gas, a reference electrode, a reference-gas introduction section that causes a reference gas to flow to the reference electrode, and a reference-gas adjustment pump cell constituted by including the outer pump electrode and the reference electrode. The controller performs a moisture-absorption-state diagnosis process of diagnosing a moisture absorption state around the reference electrode based on a pump current flowing through the reference-gas adjustment pump cell when the reference-gas adjustment pump cell is controlled to pump out oxygen from a periphery of the reference electrode to a periphery of the outer pump electrode.

15 Claims, 6 Drawing Sheets

(58) Field of Classification Search
CPC ............... G01N 27/41; G01N 27/4163; G01N 33/0029; G01N 33/004; G01N 33/0042; G01N 33/0044; G01N 33/0047; G01N 27/406; G01N 27/407; G01N 27/417; G01N 27/0467
USPC ..... 73/1.02, 1.03, 1.06, 23.31, 23.32, 31.05, 73/31.06; 205/335, 337; 429/90, 427, 429/430–432, 449; 422/83
See application file for complete search history.

GAS SENSOR AND METHOD OF DIAGNOSING MOISTURE ABSORPTION STATE OF GAS SENSOR

The present application claims priority of Japanese Patent Application No. 2021-203831 filed on Dec. 16, 2021, and Japanese Patent Application No. 2022-191635 filed on Nov. 30, 2022 the entire contents of which are incorporated herein by reference.

BACKGROUND OF THE INVENTION

1. Field of the Invention

The present invention relates to a gas sensor and a method of diagnosing a moisture absorption state of the gas sensor.

2. Description of the Related Art

A known sensor element in related art is used for a gas sensor that detects the concentration of a specific gas such as NOx in a measurement-object gas such as an exhaust gas of an automobile. For example, Patent Literature 1 discloses a sensor element including an element body having an oxygen-ion-conductive solid electrolyte layer and provided therein with a measurement-object gas flow section that introduces a measurement-object gas and causes the measurement-object gas to flow therethrough, a measurement electrode disposed on the inner peripheral surface of the measurement-object gas flow section, a reference electrode disposed inside the element body, and a reference-gas introduction section that introduces a reference gas (e.g., atmospheric gas) serving as a reference for detection of a specific gas concentration in the measurement-object gas and causes the reference gas to flow to the reference electrode. The reference-gas introduction section has a porous reference-gas introduction layer. The specific gas concentration in the measurement-object gas can be detected based on an electromotive force occurring between the reference electrode and the measurement electrode of this sensor element.

CITATION LIST

Patent Literature

PTL 1: JP 2020-094899 A

SUMMARY OF THE INVENTION

There has been a case where the reference-gas introduction section adsorbs external water, for example, in a period in which the sensor element is not driven. Because the sensor element is heated when the driving is started, the water in the reference-gas introduction section becomes a gas and is released outward from the reference-gas introduction section. However, until the water is released, the water in the gaseous state exists, causing the oxygen concentration around the reference electrode to decrease. As a result, the detection accuracy of the specific gas concentration may decrease until the water is released. Thus, it has been desirable to diagnose a moisture absorption state around the reference electrode.

The present invention has been made to solve the aforementioned problems, and a main object thereof is to diagnose a moisture absorption state around a reference electrode.

In order to achieve the aforementioned main object, the present invention employs the following solutions.

A gas sensor according to the present invention is a gas sensor that detects a specific gas concentration in a measurement-object gas, the gas sensor including: a sensor element having an element body including an oxygen-ion-conductive solid electrolyte layer and provided with a measurement-object gas flow section therein, the measurement-object gas flow section introducing the measurement-object gas and causing the measurement-object gas to flow therethrough, a measurement electrode disposed in the measurement-object gas flow section, a measurement-object-gas side electrode provided on the element body so that the measurement-object-gas side electrode comes into contact with the measurement-object gas, a reference electrode disposed inside the element body, a reference-gas introduction section that causes a reference gas serving as a reference for the detection of the specific gas concentration in the measurement-object gas to flow from outside the element body to the reference electrode, and a reference-gas adjustment pump cell constituted by including the measurement-object-gas side electrode and the reference electrode; and a controller that performs a moisture-absorption-state diagnosis process of diagnosing a moisture absorption state around the reference electrode based on a pump current flowing through the reference-gas adjustment pump cell when the reference-gas adjustment pump cell is controlled to pump out oxygen from a periphery of the reference electrode to a periphery of the measurement-object-gas side electrode.

With the gas sensor, the controller diagnoses the moisture absorption state around the reference electrode based on the pump current flowing through the reference-gas adjustment pump cell when the reference-gas adjustment pump cell is controlled to pump out the oxygen from the periphery of the reference electrode to the periphery of the measurement-object-gas side electrode. In this case, the pump current flowing when the reference-gas adjustment pump cell pumps out the oxygen from the periphery of the reference electrode to the periphery of the measurement-object-gas side electrode changes depending on the amount of moisture around the reference electrode. Accordingly, it is possible to diagnose the moisture absorption state around the reference electrode based on the pump current. The controller may determine whether the amount of moisture around the reference electrode is large in the moisture-absorption-state diagnosis process.

In the gas sensor according to the present invention, the controller may diagnose the moisture absorption state around the reference electrode based on the pump current when a predetermined control voltage higher than voltages in a limiting current region of the reference-gas adjustment pump cell is applied between the measurement-object-gas side electrode and the reference electrode in the moisture-absorption-state diagnosis process. When a voltage higher than the voltages in the limiting current region is applied, the moisture around the reference electrode is likely to be decomposed. Thus, the amount of moisture around the reference electrode is likely to affect the pump current. Accordingly, by using the pump current when such a voltage is applied, it is possible to more appropriately diagnose the moisture absorption state of the reference electrode.

In this case, the controller may diagnose the moisture absorption state around the reference electrode based on a comparison between the pump current and a limiting current of the reference-gas adjustment pump cell in the moisture-absorption-state diagnosis process. The difference between the pump current and the limiting current increases as the amount of moisture around the reference electrode increases. Thus, it is possible to more appropriately diagnose the moisture absorption state around the reference electrode by comparing the pump current with the limiting current. In this case, the controller may diagnose the moisture absorption state around the reference electrode based on a difference or a ratio between the pump current and the limiting current in the moisture-absorption-state diagnosis process.

In the gas sensor according to the present invention of the aspect that compares the pump current with the limiting current, the controller may include a storage unit that stores a value of the limiting current, and the controller may compare the pump current with the limiting current stored in the storage unit in the moisture-absorption-state diagnosis process. Accordingly, it is not necessary to measure the limiting current in the moisture-absorption-state diagnosis process.

In the gas sensor according to the present invention of the aspect that compares the pump current with the limiting current, the controller may compare the pump current with the limiting current measured by applying a voltage in the limiting current region to the reference-gas adjustment pump cell in the moisture-absorption-state diagnosis process. In this manner, if not only the pump current but also the limiting current is measured in the moisture-absorption-state diagnosis process, the diagnosis can be performed with higher accuracy.

In the gas sensor according to the present invention, the predetermined control voltage may be a voltage between 0.8 V and 1.5 V inclusive. As long as the control voltage is a value of 0.8 V or higher, the pump current when a voltage in this range is applied is likely to change depending on the amount of moisture around the reference electrode, and thus it is appropriate for performing the moisture-absorption-state diagnosis process. When the control voltage is 1.5 V or lower, blackening of the sensor element can be suppressed.

In the gas sensor according to the present invention, the gas sensor may include a heater that heats the element body, and the controller may perform the moisture-absorption-state diagnosis process after electricity is applied to the heater and a temperature of the heater reaches a predetermined temperature or higher. Accordingly, since the moisture-absorption-state diagnosis process is performed after the temperature of the heater is increased, the reference-gas adjustment pump cell can be operated in a state where the solid electrolyte layer is activated and oxygen ion conductivity is exhibited. Thus, the moisture-absorption-state diagnosis process can be executed at an appropriate timing.

A method of diagnosing a moisture absorption state of a gas sensor according to the present invention is a method of diagnosing a moisture absorption state of a gas sensor that detects a specific gas concentration in a measurement-object gas. The gas sensor includes a sensor element having an element body including an oxygen-ion-conductive solid electrolyte layer and provided with a measurement-object gas flow section therein, the measurement-object gas flow section introducing the measurement-object gas and causing the measurement-object gas to flow therethrough, a measurement electrode disposed in the measurement-object gas flow section, a measurement-object-gas side electrode provided on the element body so that the measurement-object-gas side electrode comes into contact with the measurement-object gas, a reference electrode disposed inside the element body, a reference-gas introduction section that causes a reference gas serving as a reference for the detection of the specific gas concentration in the measurement-object gas to flow from outside the element body to the reference electrode, and a reference-gas adjustment pump cell constituted by including the measurement-object-gas side electrode and the reference electrode. The method includes: a moisture-absorption-state diagnosis process of diagnosing a moisture absorption state around the reference electrode based on a pump current flowing through the reference-gas adjustment pump cell when the reference-gas adjustment pump cell is controlled to pump out oxygen from a periphery of the reference electrode to a periphery of the measurement-object-gas side electrode.

With the method of diagnosing the moisture absorption state of the gas sensor, similarly to the above-described gas sensor, it is possible to diagnose the moisture absorption state around the reference electrode. In the method of diagnosing the moisture absorption state of the gas sensor, any of the various aspects of the gas sensor described above may be employed, and a process for implementing any of the functions of the gas sensor described above may be added.

DETAILED DESCRIPTION OF THE INVENTION

Figure 1:
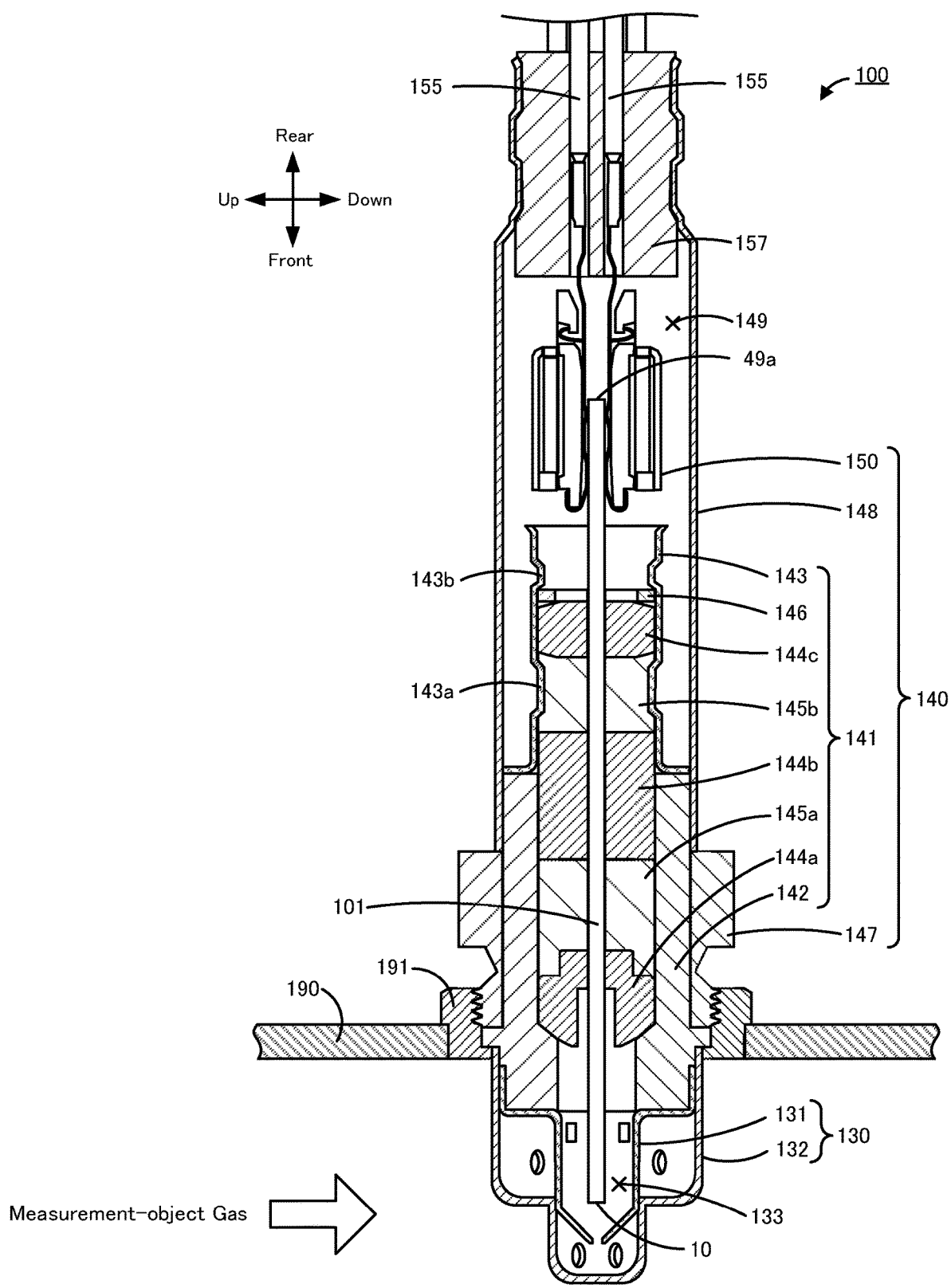
FIG. 1 is a vertical sectional view of a gas sensor 100.
Figure 2:
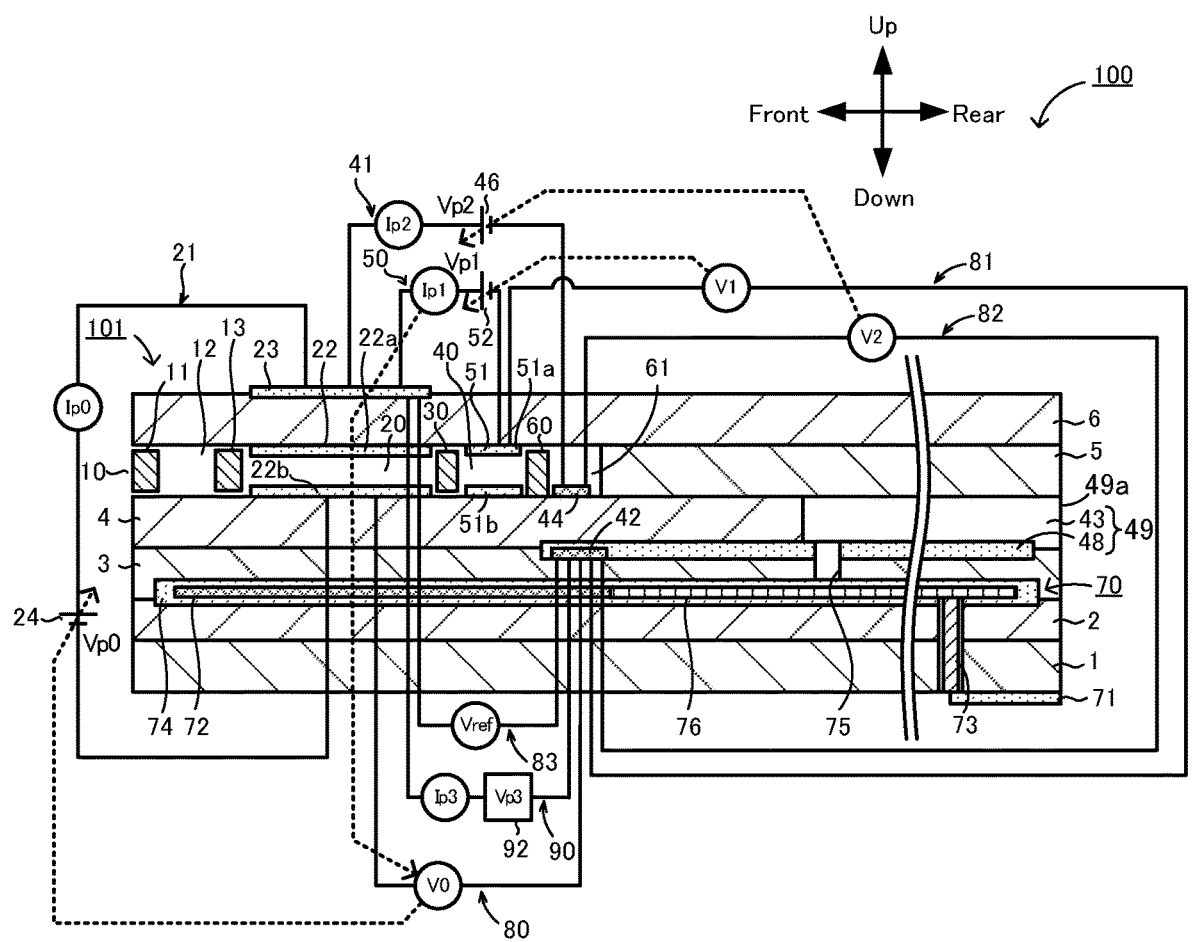
FIG. 2 is a schematic cross-sectional view schematically illustrating an example of the configuration of a sensor element 101.
Figure 3:
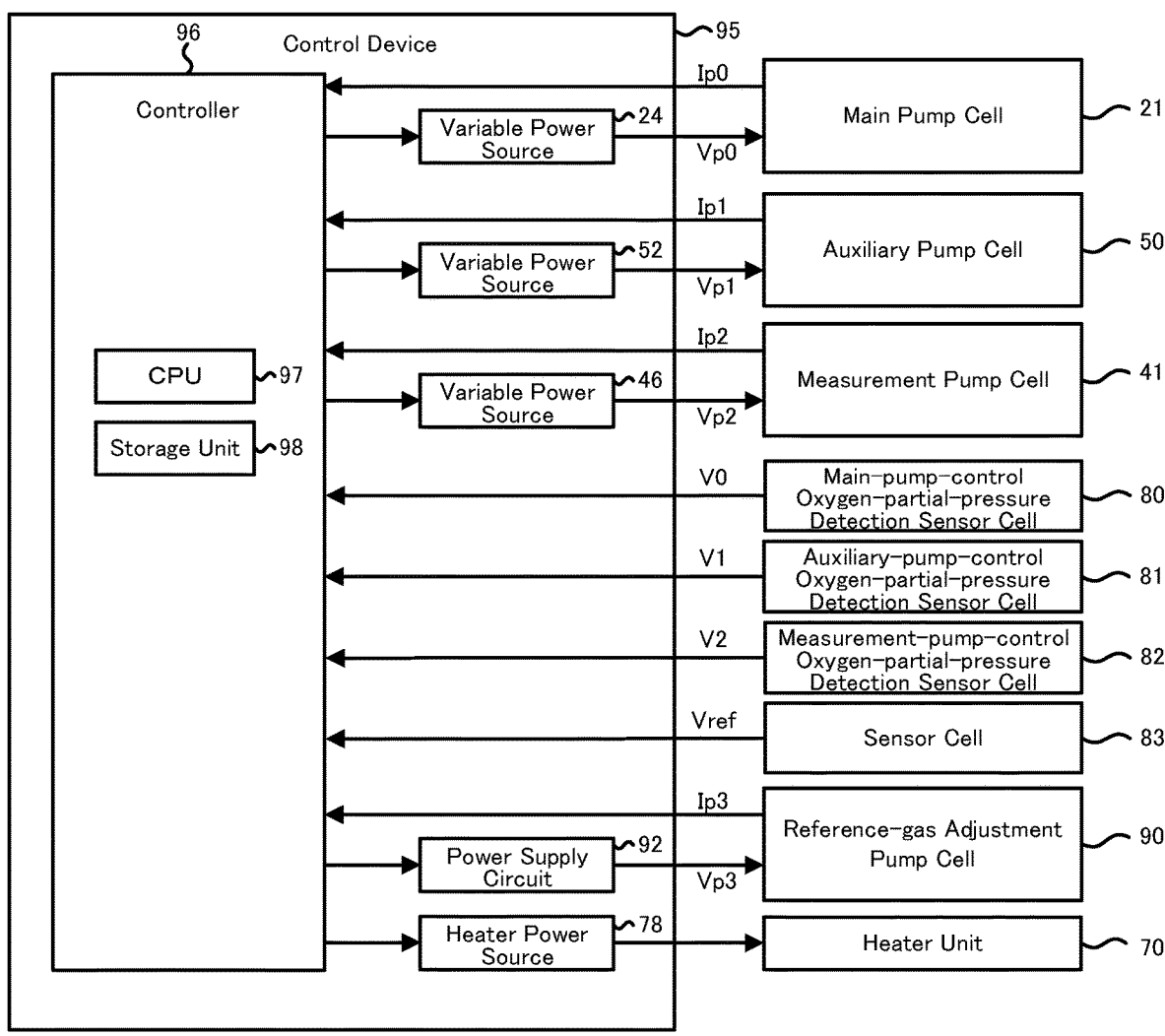
FIG. 3 is a block diagram illustrating an electrical connection relationship between a control device 95 and each cell.

Next, embodiments of the present invention will be described with reference to the drawings. FIG. 1 is a vertical sectional view of a gas sensor 100 according to an embodiment of the present invention. FIG. 2 is a schematic cross-sectional view schematically illustrating an example of the configuration of a sensor element 101 included in the gas sensor 100. FIG. 3 is a block diagram illustrating an electrical connection relationship between a control device 95 and each cell. The sensor element 101 has a long rectangular-prismatic shape. The longitudinal direction (i.e., the left-right direction in FIG. 2) of the sensor element 101 is defined as a front-rear direction, and the thickness direction (i.e., the up-down direction in FIG. 2) of the sensor element 101 is defined as an up-down direction. Furthermore, the width direction (i.e., a direction orthogonal to the front-rear direction and the up-down direction) of the sensor element 101 is defined as a left-right direction.

As shown in FIG. 1, the gas sensor 100 includes the sensor element 101, a protection cover 130 that protects the front end of the sensor element 101, and a sensor assembly 140 including a connector 150 conductive with the sensor element 101. The gas sensor 100 is attached to a pipe 190, such as an exhaust gas pipe of a vehicle, as shown in the drawing, and is used for measuring the concentration of a specific gas, such as $NO_x$ or $O_2$, contained in exhaust gas as a measurement-object gas. In this embodiment, the gas sensor 100 measures the $NO_x$ concentration as the specific gas concentration.

The protection cover 130 includes a bottomed cylindrical inner protection cover 131 that covers the front end of the sensor element 101, and a bottomed cylindrical outer protection cover 132 that covers the inner protection cover 131. The inner protection cover 131 and the outer protection cover 132 each have a plurality of holes for causing the measurement-object gas to flow into the protection cover 130. A sensor element chamber 133 is provided as a space surrounded by the inner protection cover 131, and the front end of the sensor element 101 is disposed in this sensor element chamber 133.

The sensor assembly 140 includes an element sealing unit 141 that seals and secures the sensor element 101, a bolt 147 attached to the element sealing unit 141, an outer cylinder 148, and the connector 150 that is in contact with and electrically connected to connector electrodes (not shown) provided on surfaces (i.e., upper and lower surfaces) at the rear end of the sensor element 101 (only a heater connector electrode 71 to be described later is shown in FIG. 2).

The element sealing unit 141 includes a cylindrical main fitting 142, a cylindrical inner cylinder 143 welded and secured coaxially to the main fitting 142, and ceramic supporters 144a to 144c, green compacts 145a and 145b, and a metal ring 146 that are sealed in a through-hole within the main fitting 142 and the inner cylinder 143. The sensor element 101 is located on the central axis of the element sealing unit 141 and extends through the element sealing unit 141 in the front-rear direction. The inner cylinder 143 has a reduced-diameter section 143a for pressing the green compact 145b toward the central axis of the inner cylinder 143 and a reduced-diameter section 143b for pressing the ceramic supporters 144a to 144c and the green compacts 145a and 145b forward via the metal ring 146. The green compacts 145a and 145b are compressed between the main fitting 142, the inner cylinder 143, and the sensor element 101 by the pressing forces from the reduced-diameter sections 143a and 143b, so that the green compacts 145a and 145b seal between the sensor element chamber 133 in the protection cover 130 and a space 149 in the outer cylinder 148, and also secure the sensor element 101.

The bolt 147 is secured coaxially to the main fitting 142 and has a male threaded section around the outer peripheral surface thereof. The male threaded section of the bolt 147 is inserted into a securing member 191 having a female threaded section in the inner peripheral surface thereof and welded to the pipe 190. Accordingly, the gas sensor 100 is secured to the pipe 190 in a state where the front end of the sensor element 101 and a part of the protection cover 130 of the gas sensor 100 protrude into the pipe 190.

The outer cylinder 148 covers the inner cylinder 143, the sensor element 101, and the connector 150, and a plurality of lead wires 155 connected to the connector 150 are routed outward from the rear end. The lead wires 155 are conductive with electrodes (to be described later) of the sensor element 101 via the connector 150. A gap between the outer cylinder 148 and the lead wires 155 is sealed by a rubber stopper 157. The space 149 in the outer cylinder 148 is filled with a reference gas (i.e., atmospheric gas in this embodiment). The rear end of the sensor element 101 is disposed in this space 149.

As shown in FIG. 2, the sensor element 101 has a layered body obtained by stacking six layers, namely, a first substrate layer 1, a second substrate layer 2, a third substrate layer 3, a first solid electrolyte layer 4, a spacer layer 5, and a second solid electrolyte layer 6 that are formed of oxygen-ion-conductive solid electrolyte layers composed of, for example, zirconia ($ZrO_2$), in that order from below in the drawing. The solid electrolyte used for forming each of these six layers is dense and hermetic. For example, the sensor element 101 is manufactured by performing predetermining processing and printing of a circuit pattern on ceramic green sheets corresponding to the individual layers, subsequently stacking the sheets, and then combining the sheets by calcination.

At one end (i.e., left end in FIG. 2) of the sensor element 101, a gas inlet 10, a first diffusion controlling section 11, a buffer space 12, a second diffusion controlling section 13, a first internal cavity 20, a third diffusion controlling section 30, a second internal cavity 40, a fourth diffusion controlling section 60, and a third internal cavity 61 are provided next to one another between the lower surface of the second solid electrolyte layer 6 and the upper surface of the first solid electrolyte layer 4 in a communicating manner in that order.

The gas inlet 10, the buffer space 12, the first internal cavity 20, the second internal cavity 40, and the third internal cavity 61 are spaces formed inside the sensor element 101 by hollowing out the spacer layer 5 and each have an upper side partitioned by the lower surface of the second solid electrolyte layer 6, a lower side partitioned by the upper surface of the first solid electrolyte layer 4, and lateral sides partitioned by the side surfaces of the spacer layer 5.

The first diffusion controlling section 11, the second diffusion controlling section 13, and the third diffusion controlling section 30 are each provided as two horizontally-long slits (the openings of which extend longitudinally in a direction orthogonal to the drawing). The fourth diffusion controlling section 60 is provided as a single horizontally-long slit (the opening of which extends longitudinally in the direction orthogonal to the drawing) serving as a gap with respect to the lower surface of the second solid electrolyte layer 6. A section extending from the gas inlet 10 to the third internal cavity 61 is also referred to as a measurement-object gas flow section.

The sensor element 101 includes a reference-gas introduction section 49 that allows the reference gas to flow from outside the sensor element 101 to a reference electrode 42 when the $NO_x$ concentration is to be measured. The reference-gas introduction section 49 has a reference-gas introduction space 43 and a reference-gas introduction layer 48. The reference-gas introduction space 43 is provided inward from the rear end surface of the sensor element 101. The reference-gas introduction space 43 is provided at a position between the upper surface of the third substrate layer 3 and the lower surface of the spacer layer 5 and has lateral sides partitioned by the side surfaces of the first solid electrolyte layer 4. The reference-gas introduction space 43 has an opening at the rear end surface of the sensor element 101, and this opening functions as an entrance 49a for the reference-gas introduction section 49. The entrance 49a is exposed to the space 149 (see FIG. 1). The reference gas is introduced into the reference-gas introduction space 43 through this entrance 49a. The reference-gas introduction section 49 introduces the reference gas to the reference electrode 42 while applying a predetermined diffusion resistance to the reference gas introduced through the entrance 49a. In this embodiment, the reference gas is the atmospheric gas (i.e., atmosphere in the space 149 in FIG. 1).

The reference-gas introduction layer 48 is provided between the upper surface of the third substrate layer 3 and the lower surface of the first solid electrolyte layer 4. The reference-gas introduction layer 48 is a porous body composed of a ceramic material, such as alumina. The upper surface of the reference-gas introduction layer 48 is partially exposed to the reference-gas introduction space 43. The reference-gas introduction layer 48 is provided to cover the reference electrode 42. The reference-gas introduction layer 48 allows the reference gas to flow from the reference-gas introduction space 43 to the reference electrode 42.

The reference electrode 42 is interposed between the upper surface of the third substrate layer 3 and the first solid electrolyte layer 4 and is surrounded by the reference-gas introduction layer 48 connected to the reference-gas introduction space 43, as mentioned above. Furthermore, as will be described later, the reference electrode 42 can be used for measuring the oxygen concentration (oxygen partial pressure) in the first internal cavity 20, the second internal cavity 40, and the third internal cavity 61. The reference electrode 42 is provided as a porous cermet electrode (e.g., a cermet electrode composed of Pt and $ZrO_2$).

In the measurement-object gas flow section, the gas inlet 10 is open to an external space, such that the measurement-object gas is taken into the sensor element 101 from the external space through the gas inlet 10. The first diffusion controlling section 11 applies a predetermined diffusion resistance to the measurement-object gas taken in through the gas inlet 10. The buffer space 12 is provided for guiding the measurement-object gas introduced by the first diffusion controlling section 11 to the second diffusion controlling section 13. The second diffusion controlling section 13 applies a predetermined diffusion resistance to the measurement-object gas introduced to the first internal cavity 20 from the buffer space 12. When the measurement-object gas is to be introduced to the first internal cavity 20 from outside the sensor element 101, the measurement-object gas quickly taken into the sensor element 101 through the gas inlet 10 due to pressure fluctuation (i.e., pulsation of exhaust pressure if the measurement-object gas is exhaust gas of an automobile) of the measurement-object gas in the external space is not directly introduced to the first internal cavity 20 but is introduced to the first internal cavity 20 after the pressure fluctuation of the measurement-object gas is negated by traveling through the first diffusion controlling section 11, the buffer space 12, and the second diffusion controlling section 13. Accordingly, the pressure fluctuation of the measurement-object gas to be introduced to the first internal cavity 20 can be made substantially negligible. The first internal cavity 20 is provided as a space for adjusting the oxygen partial pressure in the measurement-object gas introduced via the second diffusion controlling section 13. The oxygen partial pressure is adjusted by actuating a main pump cell 21.

The main pump cell 21 is an electrochemical pump cell constituted of an inner pump electrode 22 having a ceiling electrode 22a provided substantially over the entire lower surface of the second solid electrolyte layer 6 facing the first internal cavity 20, an outer pump electrode 23 provided in a region corresponding to the ceiling electrode 22a on the upper surface of the second solid electrolyte layer 6 in a manner such that the outer pump electrode 23 is exposed to the external space (i.e., the sensor element chamber 133 in FIG. 1), and the second solid electrolyte layer 6 interposed between these electrodes.

The inner pump electrode 22 is provided astride the upper and lower solid electrolyte layers (i.e., the second solid electrolyte layer 6 and the first solid electrolyte layer 4) that define the first internal cavity 20, and the spacer layer 5 that provides sidewalls. In detail, the lower surface of the second solid electrolyte layer 6 that provides a ceiling surface for the first internal cavity 20 is provided with the ceiling electrode 22a, the upper surface of the first solid electrolyte layer 4 that provides a bottom surface is provided with a bottom electrode 22b, and side electrodes (not shown) connecting the ceiling electrode 22a and the bottom electrode 22b are provided on sidewalls (inner surfaces) of the spacer layer 5 that serve as opposite sidewalls for the first internal cavity 20, such that the inner pump electrode 22 is disposed in a tunnel-like structure in a region where the side electrodes are arranged.

The inner pump electrode 22 and the outer pump electrode 23 are provided as porous cermet electrodes (e.g., cermet electrodes composed of Pt and $ZrO_2$ and containing 1% of Au). The inner pump electrode 22 that comes into contact with the measurement-object gas is formed by using a material with a lowered reduction ability against the $NO_x$ component in the measurement-object gas.

In the main pump cell 21, a desired voltage Vp0 is applied between the inner pump electrode 22 and the outer pump electrode 23 so that a pump current Ip0 flows in the positive direction or the negative direction between the inner pump electrode 22 and the outer pump electrode 23, whereby the oxygen in the first internal cavity 20 can be pumped out to the external space or the oxygen in the external space can be pumped into the first internal cavity 20.

Furthermore, in order to detect the oxygen concentration (oxygen partial pressure) in the atmosphere within the first internal cavity 20, the inner pump electrode 22, the second solid electrolyte layer 6, the spacer layer 5, the first solid electrolyte layer 4, the third substrate layer 3, and the reference electrode 42 constitute an electrochemical sensor cell, that is, a main-pump-control oxygen-partial-pressure detection sensor cell 80.

The oxygen concentration (oxygen partial pressure) in the first internal cavity 20 can be determined by measuring an electromotive force (voltage V0) in the main-pump-control oxygen-partial-pressure detection sensor cell 80. Furthermore, feedback control is performed on the pump voltage Vp0 of a variable power source 24 so that the voltage V0 becomes a target value, whereby the pump current Ip0 is controlled. Accordingly, the oxygen concentration in the first internal cavity 20 can be maintained at a predetermined fixed value.

The third diffusion controlling section 30 applies a predetermined diffusion resistance to the measurement-object gas, the oxygen concentration (oxygen partial pressure) of which has been controlled in the first internal cavity 20 in accordance with the operation of the main pump cell 21, and guides the measurement-object gas to the second internal cavity 40.

The second internal cavity 40 is provided as a space where an auxiliary pump cell 50 further adjusts the oxygen partial pressure of the measurement-object gas that has preliminarily undergone oxygen concentration (oxygen partial pressure) adjustment in the first internal cavity 20 and that has subsequently been introduced via the third diffusion controlling section 30. Accordingly, the oxygen concentration in the second internal cavity 40 can be maintained at a fixed level with high accuracy, thereby allowing for highly-accurate $NO_x$ concentration measurement in the gas sensor 100.

The auxiliary pump cell 50 is an auxiliary electrochemical pump cell constituted of an auxiliary pump electrode 51 having a ceiling electrode 51a provided substantially over the entire lower surface of the second solid electrolyte layer 6 facing the second internal cavity 40, the outer pump electrode 23 (but not limited to the outer pump electrode 23 and may possibly be an appropriate electrode at the outer side of the sensor element 101), and the second solid electrolyte layer 6.

The auxiliary pump electrode 51 is disposed within the second internal cavity 40 in a tunnel-like structure similar to the aforementioned inner pump electrode 22 provided in the first internal cavity 20. Specifically, the tunnel-like structure is provided such that the second solid electrolyte layer 6 that provides a ceiling surface for the second internal cavity 40 is provided with the ceiling electrode 51a, the first solid electrolyte layer 4 that provides a bottom surface for the second internal cavity 40 is provided with a bottom electrode 51b, and side electrodes (not shown) that connect the ceiling electrode 51a and the bottom electrode 51b are provided on opposite wall surfaces of the spacer layer 5 that provide sidewalls for the second internal cavity 40. The auxiliary pump electrode 51 is similar to the inner pump electrode 22 in being formed by using a material with a lowered reduction ability against the $NO_x$ component in the measurement-object gas.

In the auxiliary pump cell 50, a desired voltage Vp1 is applied between the auxiliary pump electrode 51 and the outer pump electrode 23 so that the oxygen in the atmosphere within the second internal cavity 40 can be pumped out to the external space or the oxygen can be pumped into the second internal cavity 40 from the external space.

Furthermore, in order to control the oxygen partial pressure in the atmosphere within the second internal cavity 40, the auxiliary pump electrode 51, the reference electrode 42, the second solid electrolyte layer 6, the spacer layer 5, the first solid electrolyte layer 4, and the third substrate layer 3 constitute an electrochemical sensor cell, that is, an auxiliary-pump-control oxygen-partial-pressure detection sensor cell 81.

The auxiliary pump cell 50 performs pumping in accordance with a variable power source 52 that is voltage-controlled based on an electromotive force (voltage V1) detected by the auxiliary-pump-control oxygen-partial-pressure detection sensor cell 81. Accordingly, the oxygen partial pressure in the atmosphere within the second internal cavity 40 is controlled to a low partial pressure that substantially has no effect on $NO_x$ measurement.

In addition, a pump current Ip1 is used for controlling the electromotive force of the main-pump-control oxygen-partial-pressure detection sensor cell 80. In detail, the pump current Ip1 is input as a control signal to the main-pump-control oxygen-partial-pressure detection sensor cell 80, and the voltage V0 is controlled to the aforementioned target value, whereby the gradient of the oxygen partial pressure in the measurement-object gas introduced to the second internal cavity 40 from the third diffusion controlling section 30 is controlled such that the gradient is constantly fixed. When the gas sensor 100 is used as a $NO_x$ sensor, the oxygen concentration within the second internal cavity 40 is maintained at a fixed value of about 0.001 ppm in accordance with the functions of the main pump cell 21 and the auxiliary pump cell 50.

The fourth diffusion controlling section 60 applies a predetermined diffusion resistance to the measurement-object gas, the oxygen concentration (oxygen partial pressure) of which has been controlled in the second internal cavity 40 in accordance with the operation of the auxiliary pump cell 50, and guides the measurement-object gas to the third internal cavity 61. The fourth diffusion controlling section 60 has a role of limiting the amount of $NO_x$ flowing into the third internal cavity 61.

The third internal cavity 61 is provided as a space where a process for measuring the nitrogen oxide ($NO_x$) concentration in the measurement-object gas is performed on the measurement-object gas that has preliminarily undergone oxygen concentration (oxygen partial pressure) adjustment in the second internal cavity 40 and that has subsequently been introduced via the fourth diffusion controlling section 60. The $NO_x$ concentration is measured mainly in the third internal cavity 61 in accordance with the operation of a measurement pump cell 41.

The measurement pump cell 41 measures the $NO_x$ concentration in the measurement-object gas within the third internal cavity 61. The measurement pump cell 41 is an electrochemical pump cell constituted of a measurement electrode 44 provided on the upper surface of the first solid electrolyte layer 4 facing the third internal cavity 61, the outer pump electrode 23, the second solid electrolyte layer 6, the spacer layer 5, and the first solid electrolyte layer 4. The measurement electrode 44 is a porous cermet electrode composed of a material with a higher reduction ability against the $NO_x$ component in the measurement-object gas than the inner pump electrode 22. The measurement electrode 44 also functions as a $NO_x$ reduction catalyst that reduces the $NO_x$ existing in the atmosphere within the third internal cavity 61.

In the measurement pump cell 41, oxygen produced as a result of decomposition of the nitrogen oxide in the atmosphere surrounding the measurement electrode 44 is pumped out, and the amount of oxygen produced can be detected as a pump current Ip2.

Furthermore, in order to detect the oxygen partial pressure around the measurement electrode 44, the first solid electrolyte layer 4, the third substrate layer 3, the measurement electrode 44, and the reference electrode 42 constitute an electrochemical sensor cell, that is, a measurement-pump-control oxygen-partial-pressure detection sensor cell 82. A variable power source 46 is controlled based on an electromotive force (voltage V2) detected by the measurement-pump-control oxygen-partial-pressure detection sensor cell 82.

The measurement-object gas introduced to the second internal cavity 40 reaches the measurement electrode 44 in the third internal cavity 61 via the fourth diffusion controlling section 60 under a condition where the oxygen partial pressure is controlled. The nitrogen oxide in the measurement-object gas surrounding the measurement electrode 44 is reduced ($2NO \rightarrow N_2 + O_2$), so that oxygen is produced. Then, the produced oxygen is to undergo pumping by the measurement pump cell 41. During the pumping of the oxygen, a voltage Vp2 of the variable power source 46 is controlled such that the voltage V2 detected by the measurement-pump-control oxygen-partial-pressure detection sensor cell 82 is a fixed value (i.e., a target value). Because the amount of oxygen produced around the measurement electrode 44 is proportional to the concentration of the nitrogen oxide in the measurement-object gas, the nitrogen oxide concentration in the measurement-object gas is calculated by using the pump current Ip2 in the measurement pump cell 41.

Furthermore, the second solid electrolyte layer 6, the spacer layer 5, the first solid electrolyte layer 4, the third substrate layer 3, the outer pump electrode 23, and the reference electrode 42 constitute an electrochemical sensor cell 83. The oxygen partial pressure in the measurement-object gas outside the sensor can be detected in accordance with an electromotive force (voltage Vref) obtained by the sensor cell 83.

Moreover, the second solid electrolyte layer 6, the spacer layer 5, the first solid electrolyte layer 4, the third substrate layer 3, the outer pump electrode 23, and the reference electrode 42 constitute an electrochemical reference-gas adjustment pump cell 90. The reference-gas adjustment pump cell 90 performs oxygen pumping by receiving a control current (pump current Ip3) flowing in accordance with a control voltage (voltage Vp3) applied by a power supply circuit 92 connected between the outer pump electrode 23 and the reference electrode 42. Accordingly, the reference-gas adjustment pump cell 90 can pump in the oxygen from the space of the periphery of the outer pump electrode 23 (the sensor element chamber 133 in FIG. 1) to the periphery of the reference electrode 42 or pump out the oxygen from the periphery of the reference electrode 42 to the periphery of the outer pump electrode 23.

In the gas sensor 100 having the above configuration, the measurement pump cell 41 receives the measurement-object gas whose oxygen partial pressure is constantly maintained at a fixed low value (i.e., a value that substantially has no effect on $NO_x$ measurement) as a result of actuation of the main pump cell 21 and the auxiliary pump cell 50. Thus, the $NO_x$ concentration in the measurement-object gas can be ascertained based on the pump current Ip2 flowing as a result of oxygen produced by $NO_x$ reduction being pumped out by the measurement pump cell 41 substantially in proportion to the $NO_x$ concentration in the measurement-object gas.

Furthermore, in order to enhance oxygen ion conductivity of the solid electrolyte, the sensor element 101 includes a heater unit 70 having a role of temperature adjustment for keeping the sensor element 101 warm by heating the sensor element 101. The heater unit 70 includes a heater connector electrode 71, a heater 72, a through-hole 73, a heater insulation layer 74, a pressure release hole 75, and a lead wire 76.

The heater connector electrode 71 is provided in contact with the lower surface of the first substrate layer 1. By being connected to an external power source, the heater connector electrode 71 can supply electricity to the heater unit 70 from the outside.

The heater 72 is an electrical resistor interposed between the second substrate layer 2 and the third substrate layer 3 from above and below. The heater 72 is connected to the heater connector electrode 71 via the lead wire 76 and the through-hole 73, and generates heat by being supplied with electricity from the outside via the heater connector electrode 71, thereby heating and maintaining the temperature of the solid electrolyte constituting the sensor element 101.

Furthermore, the heater 72 is embedded in the entire region from the first internal cavity 20 to the third internal cavity 61, and is capable of adjusting the entire sensor element 101 to a temperature at which the aforementioned solid electrolyte is activated.

The heater insulation layer 74 is a porous-alumina insulation layer provided on the upper and lower surfaces of the heater 72 and formed of an insulator composed of, for example, alumina. The heater insulation layer 74 is provided for the purpose of obtaining electrical insulation between the second substrate layer 2 and the heater 72, as well as electrical insulation between the third substrate layer 3 and the heater 72.

The pressure release hole 75 extends through the third substrate layer 3 and the reference-gas introduction layer 48 and is provided for the purpose of alleviating an increase in internal pressure occurring due to a temperature increase in the heater insulation layer 74.

As shown in FIG. 3, the control device 95 includes the aforementioned variable power sources 24, 46, and 52, a heater power source 78, the aforementioned power supply circuit 92, and a controller 96. The controller 96 is a microprocessor including a CPU 97, a RAM (not shown), and a storage unit 98. The storage unit 98 is a nonvolatile memory, and is a device that stores, for example, various programs and various data. The controller 96 receives the voltages V0 to V2 and the voltage Vref from the sensor cells 80 to 83. The controller 96 receives the pump currents Ip0 to Ip2 and the pump current Ip3 flowing through the pump cells 21, 50, 41, and 90. The controller 96 outputs control signals to the variable power sources 24, 46, and 52 and the power supply circuit 92 so as to control the voltages Vp0 to Vp3 output by the variable power sources 24, 46, and 52 and the power supply circuit 92, thereby controlling the pump cells 21, 41, 50, and 90. The controller 96 outputs a control signal to the heater power source 78 so as to control the electric power supplied to the heater 72 by the heater power source 78, thereby adjusting the temperature of the sensor element 101. The storage unit 98 stores target values V0*, V1*, and V2* and a target current Ip1* (to be described later). The CPU 97 of the controller 96 controls the cells 21, 41, and 50 with reference to the target values V0*, V1*, and V2* and the target current Ip1*.

The controller 96 performs an auxiliary pump control process of controlling the auxiliary pump cell 50 so that the oxygen concentration in the second internal cavity 40 becomes a target concentration. In detail, the controller 96 controls the auxiliary pump cell 50 by performing feedback control on the voltage Vp1 of the variable power source 52 so that the voltage V1 becomes a fixed value (referred to as a target value V1*). The target value V1* is determined as a value at which the oxygen concentration in the second internal cavity 40 becomes a predetermined low concentration that substantially has no effect on the measurement of NOx.

The controller 96 performs a main pump control process of controlling the main pump cell 21 so that the pump current Ip1 flowing when the auxiliary pump cell 50 adjusts the oxygen concentration in the second internal cavity 40 by the auxiliary pump control process becomes a target current (referred to as a target current Ip1*). In detail, the controller 96 sets (i.e., performs feedback control on) the target value (referred to as a target value V0*) of the voltage V0 based on the pump current Ip1 so that the pump current Ip1 flowing in accordance with the voltage Vp1 becomes the fixed target current Ip1*. The controller 96 performs feedback control on the voltage Vp0 of the variable power source 24 so that the voltage V0 becomes the target value V0* (i.e., so that the oxygen concentration in the first internal cavity 20 becomes a target concentration). By this main pump control process, the gradient of the oxygen partial pressure in the measurement-object gas introduced to the second internal cavity 40 from the third diffusion controlling section 30 is constantly fixed. The target value V0* is set to a value at which the oxygen concentration in the first internal cavity 20 is higher than 0% and is a low oxygen concentration. The pump current Ip0 flowing during the main pump control process changes in accordance with the oxygen concentration in the measurement-object gas flowing into the measurement-object gas flow section through the gas inlet 10 (i.e., the measurement-object gas around the sensor element 101).

Thus, the controller 96 can also detect the oxygen concentration in the measurement-object gas based on the pump current Ip0.

The main pump control process and the auxiliary pump control process described above are also collectively referred to as an adjustment pump control process. The first internal cavity 20 and the second internal cavity 40 are also collectively referred to as an oxygen-concentration adjustment chamber. The main pump cell 21 and the auxiliary pump cell 50 are also collectively referred to as an adjustment pump cell. When the controller 96 performs the adjustment pump control process, the adjustment pump cell adjusts the oxygen concentration in the oxygen-concentration adjustment chamber.

Furthermore, the controller 96 performs a measurement pump control process of controlling the measurement pump cell 41 so that the voltage V2 becomes a fixed value (target value) (i.e., so that the oxygen concentration in the third internal cavity 61 becomes a predetermined low concentration). In detail, the controller 96 controls the measurement pump cell 41 by performing feedback control on the voltage Vp2 of the variable power source 46 so that the voltage V2 becomes the target value V2*. By performing this measurement pump control process, oxygen is pumped out from the third internal cavity 61.

By performing the measurement pump control process, oxygen is pumped out from the third internal cavity 61 so that the oxygen produced by the reduction of NOx in the measurement-object gas in the third internal cavity 61 becomes substantially zero. Then, the controller 96 acquires the pump current Ip2 as a detection value according to the oxygen produced in the third internal cavity 61 from a specific gas (in this case, NOx), and calculates the NOx concentration in the measurement-object gas based on the pump current Ip2.

The storage unit 98 stores therein, for example, a relational expression (e.g., a linear function expression or a quadratic function expression) or a map as a correspondence relationship between the pump current Ip2 and the NOx concentration. Such a relational expression or a map can be preliminarily obtained from experiments.

The controller 96 controls the power supply circuit 92 so that the voltage Vp3 is applied to the reference-gas adjustment pump cell 90, and causes the pump current Ip3 to flow through the reference-gas adjustment pump cell 90. The controller 96 controls the magnitude or the flow direction of the pump current Ip3 by changing the magnitude or the positive or negative of the voltage Vp3. Accordingly, the controller 96 can control the movement direction of the oxygen between the reference electrode 42 and the outer pump electrode 23 (pumping in of the oxygen to the periphery of the reference electrode 42 or pumping out of the oxygen from the periphery of the reference electrode 42), and can control the movement amount of the oxygen. In this embodiment, the voltage Vp3 is set to a direct-current voltage at which the pump current Ip3 is a predetermined value (i.e., a fixed value of direct current).

The controller 96 performs a reference-gas adjustment process of controlling the reference-gas adjustment pump cell 90 so that oxygen is pumped in from the periphery of the outer pump electrode 23 to the periphery of the reference electrode 42 to adjust the oxygen concentration around the reference electrode 42. In the sensor element 101, the measurement-object gas flow section, such as the gas inlet 10, receives the measurement-object gas from the sensor element chamber 133 shown in FIG. 1. On the other hand, the reference-gas introduction section 49 in the sensor element 101 receives the reference gas (atmospheric gas) in the space 149 shown in FIG. 1. The sensor element chamber 133 and the space 149 are partitioned by the sensor assembly 140 (i.e., the green compacts 145a and 145b), and are sealed so that the gas does not flow therebetween. However, for example, in a case where the pressure of the measurement-object gas side is high, the measurement-object gas slightly enters the space 149, sometimes causing the oxygen concentration in the space 149 to decrease. In this case, if the oxygen concentration around the reference electrode 42 also decreases, the reference potential serving as the potential of the reference electrode 42 changes. Such a decrease in the oxygen concentration around the reference electrode 42 can be compensated by performing the reference-gas adjustment process.

The control device 95 including the variable power sources 24, 46, and 52 and the power supply circuit 92 shown in FIG. 2 is actually connected to each electrode inside the sensor element 101 via a lead wire (not shown) formed inside the sensor element 101, and the connector 150 and the lead wires 155 shown in FIG. 1.

During a period in which the sensor element 101 is not driven, the reference-gas introduction section 49 may absorb water outside the sensor element 101 (in the space 149 in this case). In this regard, the inventors of the present invention examined the relationship between the moisture absorption state of the reference-gas introduction section 49 and the pump current Ip3 flowing through the reference-gas adjustment pump cell 90. First, the sensor element 101 was driven by the control device 95. In detail, the sensor element 101 was heated by applying electricity to the heater 72 from the heater power source 78 in a state where the gas sensor 100 was disposed in an atmospheric gas, and the temperature of the sensor element 101 was maintained at 800° C. After waiting for 0.5 hours in this state, the gas sensor 100 in a state with a small moisture absorption amount of the reference-gas introduction section 49 was obtained. Then, the value of the pump current Ip3 when the voltage Vp3 to be applied to the reference-gas adjustment pump cell 90 by the power supply circuit 92 was gradually changed from 0 mV to 1000 mV in the state where the gas sensor 100 was disposed in the atmospheric gas was measured. The voltage Vp3 was applied in a direction in which the reference-gas adjustment pump cell 90 pumped out oxygen from the periphery of the reference electrode 42 to the periphery of the outer pump electrode 23. A relationship between a voltage Vp3 and a pump current Ip3 in the gas sensor 100 in the state with the small moisture absorption amount, which was measured as described above, is shown as a graph L1 of a solid line in FIG. 4. Next, the gas sensor 100 was stored in a thermos-hygrostat at a temperature of 40° C. and a humidity of 85% for one week to adsorb water to the reference-gas introduction section 49, thereby obtaining the gas sensor 100 in a state with a large moisture absorption amount. The gas sensor 100 was disposed in the atmospheric gas, and the temperature of the sensor element 101 was maintained at 800° C. by the heater 72. In this state, the value of the pump current Ip3 when the voltage Vp3 was gradually changed from 0 mV to 1000 mV was measured in a manner similar to described above. A relationship between a voltage Vp3 and a pump current Ip3 in the gas sensor 100 in the state with the large moisture absorption amount, which was measured as described above, is shown as a graph L2 of a broken line in FIG. 4.

Figure 4:
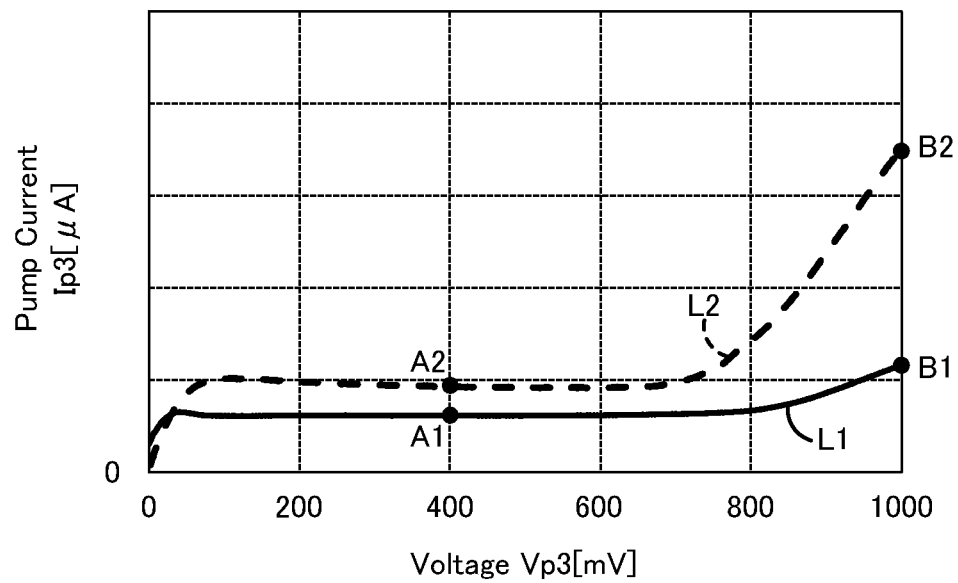
FIG. 4 is a graph showing a relationship between a voltage Vp3 and a pump current Ip3 of a reference-gas adjustment pump cell 90.

As shown in FIG. 4, in both the graph L1 and the graph L2, in a region where the voltage Vp3 was between 100 mV and 700 mV inclusive, the pump current Ip3 had a substantially fixed value even when the voltage Vp3 increased. That is, the pump current Ip3 was a limiting current. The value of the limiting current is determined in accordance with, for example, the diffusion resistance of the reference-gas introduction section 49. Such a region where the pump current Ip3 hardly changes even when the voltage Vp3 changes (in FIG. 4, for example, the region where the voltage Vp3 is between 100 mV and 700 mV inclusive) is referred to as a limiting current region. In both the graph L1 and the graph L2, in a region where the voltage Vp3 was higher than the limiting current region, the pump current Ip3 also tended to increase with an increase in the voltage Vp3. This is conceivably because as the voltage Vp3 increases, the moisture in the reference-gas introduction section 49, particularly around the reference electrode 42, is decomposed to produce oxygen, and this oxygen is also pumped out from the periphery of the reference electrode 42. In both the limiting current region and the region where the voltage Vp3 is higher than the limiting current region, the value of the pump current Ip3 in the graph L2 was larger than that in the graph L1. That is, it was confirmed that the value of the pump current Ip3 tended to be larger in the gas sensor 100 in the state with the large moisture absorption amount of the reference-gas introduction section 49. Thus, it is considered that the decomposition of the moisture around the reference electrode 42 occurs even when the voltage Vp3 in the limiting current region is applied. In particular, in the region where the voltage Vp3 was higher than the limiting current region (for example, a region where the voltage Vp3 was 800 mV or higher in FIG. 4), a difference in the value of the pump current Ip3 between the graph L2 and the graph L1 was more noticeably observed. For example, the value of the difference between a value A1 of the pump current Ip3 in the graph L1 and a value A2 of the pump current Ip3 in the graph L2 (=A2−A1) in a case where the voltage Vp3 was 400 mV within the limiting current region was larger than the value of the difference between a value B1 of the pump current Ip3 in the graph L1 and a value B2 of the pump current Ip3 in the graph L2 (=B2−B1) in a case where the voltage Vp3 was 1000 mV.

As described above, the pump current Ip3 flowing when the reference-gas adjustment pump cell 90 pumps out oxygen from the periphery of the reference electrode 42 to the periphery of the outer pump electrode 23 changes depending on the amount of moisture around the reference electrode 42. In detail, the pump current Ip3 increases as the amount of moisture around the reference electrode 42 increases. Thus, the controller 96 of this embodiment performs a moisture-absorption-state diagnosis process of diagnosing the moisture absorption state around the reference electrode 42 based on the pump current Ip3. In more detail, as an example of the moisture-absorption-state diagnosis process, the controller 96 of this embodiment performs a moisture determination process of determining whether the amount of moisture around the reference electrode 42 is large based on the pump current Ip3. Details of the moisture determination process will be described later.

Figure 5:
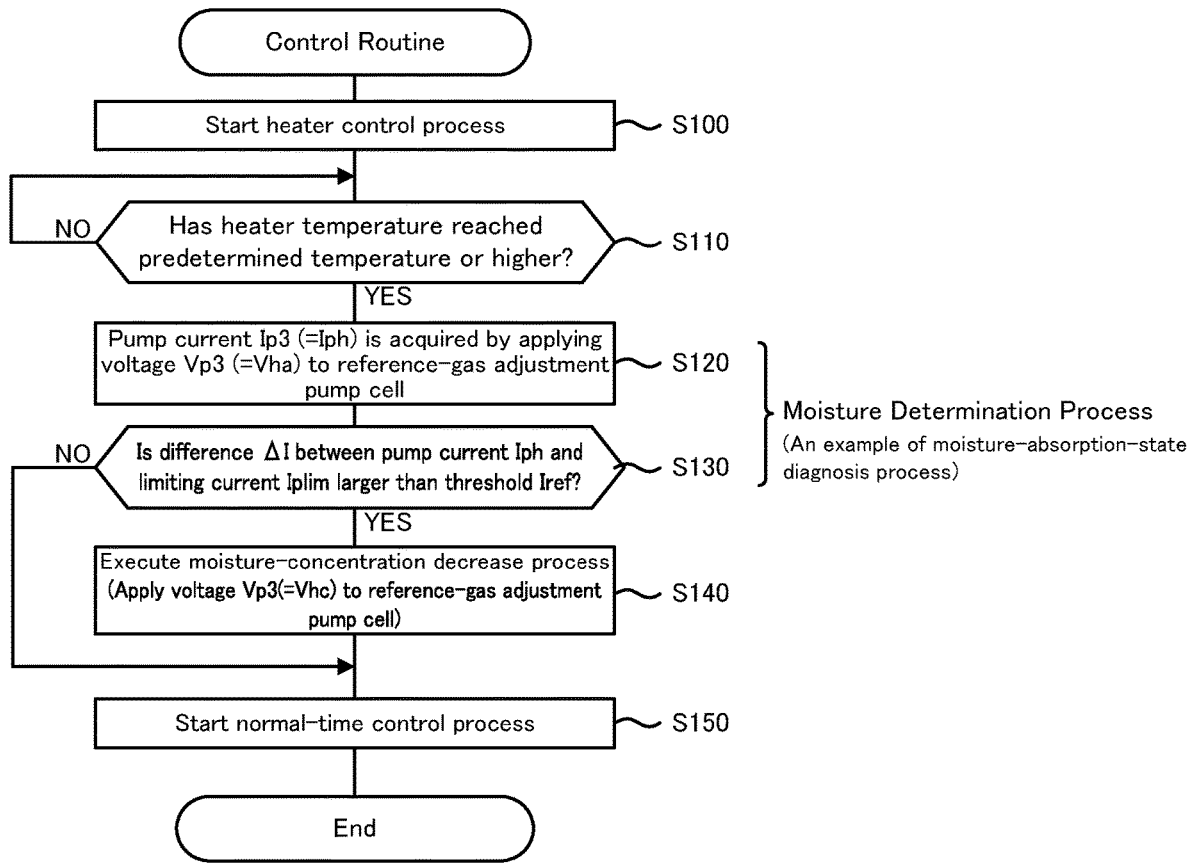
FIG. 5 is a flowchart showing an example of a control routine.

Next, an example of a process in which the controller 96 of the gas sensor 100 measures the NOx concentration will be described. FIG. 5 is a flowchart showing an example of a control routine executed by the controller 96. The controller 96 stores this routine in, for example, the storage unit 98. The controller 96 starts this control routine when receiving a start command input from, for example, an engine ECU (not shown).

When the control routine is started, the CPU 97 of the controller 96 first outputs a control signal to the heater power source 78 to start a heater control process of controlling the temperature of the heater 72 to a target temperature (for example, 800° C.) (step S100). In this case, the temperature of the heater 72 can be expressed by a linear function of the resistance value of the heater 72. Thus, in the heater control process of this embodiment, the CPU 97 calculates the resistance value of the heater 72 as a value that can be regarded as the temperature of the heater 72 (a value that can be converted into a temperature), and performs feedback control on the heater power source 78 so that the calculated resistance value becomes a target resistance value (a resistance value corresponding to a target temperature). For example, the CPU 97 can acquire the voltage of the heater 72 and the current flowing through the heater 72, and calculate the resistance value of the heater 72 based on the acquired voltage and current. The CPU 97 may calculate the resistance value of the heater 72 by, for example, a three-terminal method or a four-terminal method. The CPU 97 outputs a control signal to the heater power source 78 so that the calculated resistance value of the heater 72 becomes the target resistance value, and performs feedback control on the electric power to be supplied by the heater power source 78. When applying electricity to the heater 72, the heater power source 78 adjusts the electric power to be supplied to the heater 72 by, for example, changing the value of the voltage to be applied to the heater 72.

Then, the CPU 97 determines whether the heater temperature has reached a predetermined temperature or higher by the heater control process (step S110). The predetermined temperature is preliminarily determined as a value equal to or lower than the target temperature of the heater control process described above and stored in the storage unit 98. The predetermined temperature is preliminarily determined as a temperature at which the solid electrolyte of the sensor element 101 is activated to enable pumping of oxygen by the reference-gas adjustment pump cell 90. The predetermined temperature may be a value lower than the target temperature. The predetermined temperature may be a value of 80% or more or a value of 90% or more of the target temperature. In this embodiment, the predetermined temperature is set to a value of 90% of the target temperature. In this embodiment, since the CPU 97 uses the resistance value as a value representing the temperature of the heater 72 as described above, the determination in step S110 is also performed using the resistance value of the heater 72.

When a negative determination is made in step S110, the CPU 97 repeatedly executes step S110 and waits until a positive determination is made. That is, the CPU 97 waits until the temperature of the heater 72 reaches the predetermined temperature or higher. When the positive determination is made in step S110, the CPU 97 performs the following steps S120 and S130 as the moisture determination process.

In the moisture determination process, the CPU 97 first applies the voltage Vp3 to the reference-gas adjustment pump cell 90, and acquires the pump current Ip3 flowing at this time (step S120). The value of the voltage Vp3 applied at this time is referred to as a voltage Vha, and the value of the acquired pump current Ip3 is referred to as a pump current Iph. The voltage Vha is applied in a direction in which the reference-gas adjustment pump cell 90 pumps out oxygen from the periphery of the reference electrode 42 to the periphery of the outer pump electrode 23. The value of the voltage Vha may be a value in the range of the limiting current region described with reference to FIG. 4, but is preferably a voltage higher than the limiting current region.

The voltage Vha is preferably, for example, 0.8 V or higher. The voltage Vha may be 1.5 V or lower. In this embodiment, the voltage Vha is 1.0 V.

Then, the CPU 97 determines the moisture absorption state around the reference electrode 42 based on the acquired pump current Iph, namely, determines whether the amount of moisture around the reference electrode 42 is large (step S130). In this embodiment, the CPU 97 performs this determination based on a comparison between the pump current Iph and a limiting current Iplim of the reference-gas adjustment pump cell 90. In more detail, the CPU 97 determines whether the amount of moisture around the reference electrode 42 is large based on whether a difference ΔI between the pump current Iph and the limiting current Iplim is larger than a threshold Iref. Similarly to the limiting current described with reference to FIG. 4, the limiting current Iplim of the reference-gas adjustment pump cell 90 is a limiting current when the voltage Vp3 is applied in a direction in which the reference-gas adjustment pump cell 90 pumps out oxygen from the periphery of the reference electrode 42 to the periphery of the outer pump electrode 23. In this embodiment, the value (for example, the value A1 in FIG. 4) of the limiting current in the sensor element 101 in the state with the small moisture absorption amount of the reference-gas introduction section 49, which has been preliminarily measured by experiments, is stored in the storage unit 98 as the limiting current Iplim. Thus, the CPU 97 calculates the difference ΔI between the pump current Iph acquired in step S120 and the limiting current Iplim stored in the storage unit 98, and determines whether the difference ΔI is the threshold Iref or larger. As described above, since the pump current Iph increases as the amount of moisture around the reference electrode 42 increases, the difference ΔI also increases. Thus, for example, a threshold Iref is determined as a value of the difference ΔI in a case where the amount of moisture around the reference electrode 42 is an upper limit amount that can be regarded as having no effect on the detection accuracy of the NOx concentration. For example, in the example of FIG. 4, when the amount of moisture around the reference electrode 42 is large, the difference ΔI=B2−A1 is established, and when the amount of moisture around the reference electrode 42 is small, the difference ΔI=B1−A1 is established. Thus, a threshold Iref between both the differences is preliminarily determined.

When a positive determination is made in step S130, the CPU 97 executes a moisture-concentration decrease process of controlling the reference-gas adjustment pump cell 90 to decrease the moisture concentration around the reference electrode 42 (step S140). In the moisture-concentration decrease process of this embodiment, the CPU 97 applies the voltage Vp3 to the reference-gas adjustment pump cell 90 in the direction in which the oxygen is pumped out from the periphery of the reference electrode 42 to the periphery of the outer pump electrodes 23. The value of the voltage Vp3 at this time is referred to as a voltage Vhc. As described above, since the moisture around the reference electrode 42 can be decomposed by applying the voltage Vp3 to the reference-gas adjustment pump cell 90 so as to pump out the oxygen around the reference electrode 42, the moisture concentration around the reference electrode 42 can be decreased accordingly. The value of the voltage Vhc may be a value in the range of the limiting current region or may be a voltage higher than the limiting current region. For example, the voltage Vhc may be between 0.3 V and 1.5 V inclusive. The voltage Vhc may be 0.8 V or higher. The voltage Vhc may be 1.0 V or lower. The voltage Vhc may be the same value as the voltage Vha in the moisture determination process described above. In this embodiment, the voltage Vhc is set to 1.0 V. The execution period of the moisture-concentration decrease process is preferably between 5 seconds and 300 seconds inclusive.

In a case where a negative determination is made in step S130, or after the moisture-concentration decrease process in step S140 is executed, the CPU 97 starts a normal-time control process which is a control process at a normal time, that is, when the NOx concentration is to be measured (step S150). In detail, the CPU 97 starts the main pump control process, the auxiliary pump control process, the measurement pump control process, and the reference-gas adjustment process described above, and ends the routine. After starting the normal-time control process, the CPU 97 acquires the value of the pump current Ip2, for example, every predetermined time period, and derives the NOx concentration in the measurement-object gas based on the acquired pump current Ip2 and the correspondence relationship stored in the storage unit 98. The CPU 97 outputs the derived value of the NOx concentration to the engine ECU or stores the value in the storage unit 98.

Figure 6:
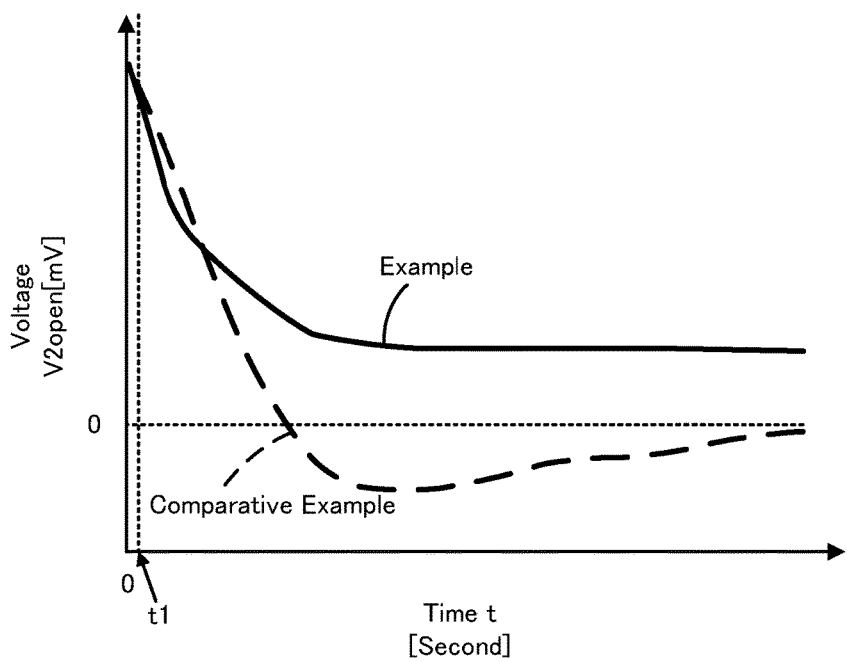
FIG. 6 is a graph showing a relationship between a time t and a voltage V2open.

With reference to FIG. 6, a description will be given of an example in which the moisture-concentration decrease process in step S140 is performed in an atmospheric gas. FIG. 6 is a graph showing a relationship between a time t and a voltage V2open in a case where the time when the temperature of the heater 72 has reached the predetermined temperature in step S110 is set to time t=0 seconds. The voltage V2open is a value of the voltage V2 in a state where no control is performed to cause a current to flow through the measurement electrode 44 and the reference electrode 42, that is, in an open state. The graph of the example indicated by a solid line in FIG. 6 was obtained as follows. First, similarly to the measurement of the graph L2 in FIG. 4, the gas sensor 100 in a state with a large moisture absorption amount of the reference-gas introduction section 49 was prepared and disposed in the atmospheric gas. Then, the heater control process was started, and the moisture-concentration decrease process was started from the timing (time t=0) at which the temperature of the heater 72 had reached the predetermined temperature in step S110, and was executed until time t=t1 in FIG. 6. The period from time t=0 to time t=t1, that is, the execution period of the moisture-concentration decrease process was set to a predetermined time period between 5 seconds and 300 seconds inclusive. The voltage Vhc was set to 1.0 V. After time t=t1, the reference-gas adjustment pump cell 90 was not operated, and the measurement electrode 44 and the reference electrode 42 were in an open state. Then, the voltage V2open was measured every 0.1 seconds after time t=0, and the graph of the example indicated by the solid line in FIG. 6 was obtained. During the period from time t=0 to time t=t1, the moisture-concentration decrease process was instantaneously stopped and the voltage V2open was measured. Also, a graph of a comparative example indicated by a broken line in FIG. 6 was obtained by performing measurement similar to the measurement in the example except that the reference-gas adjustment pump cell 90 was not operated at all and the measurement electrode 44 and the reference electrode 42 were kept in an open state.

As seen in FIG. 6, in both the example and the comparative example, it was confirmed that the voltage V2open decreased as time elapsed from time t=0, and thereafter, the voltage V2open tended to be stable. However, in the comparative example in which the moisture-concentration decrease process was not performed, the voltage V2open became stable more slowly than in the example. Also, in the comparative example, the voltage V2open was temporarily a negative value. This is conceivably because the moisture around the reference electrode 42 is heated by the heater 72 and becomes a gas, so that the oxygen concentration around the reference electrode 42 temporarily becomes lower than the oxygen concentration in the atmospheric gas. In such a state, the potential of the reference electrode 42 (reference potential) is not stable, and errors occur in the values of the voltages V0, V1, and V2 measured with reference to the reference potential. As a result, the detection accuracy of the NOx concentration decreases. In contrast, in the example in which the moisture-concentration decrease process was performed, the voltage V2open was stable earlier than in the comparative example. This is conceivably because the moisture around the reference electrode 42 is decomposed by the moisture-concentration decrease process during the period from time t=0 to time t=t1, and thus a decrease in the oxygen concentration around the reference electrode 42 caused by vaporization of the moisture is suppressed. In this case, since the reference potential becomes quickly stable, a decrease in the detection accuracy of the NOx concentration is suppressed as compared with in the comparative example. In both the example and the comparative example, the reason why the voltage V2open decreases as time elapses from time t=0 is conceivably that the thermoelectromotive force between the reference electrode 42 and the measurement electrodes 44 is included in the voltage V2open, and the thermoelectromotive force decreases as time elapses. For example, when there is a temperature variation in each of the reference electrode 42 and the measurement electrode 44, the thermoelectromotive force between the reference electrode 42 and the measurement electrode 44 increases. As the temperature in each electrode becomes uniform as time elapses, the thermoelectromotive force decreases.

The correspondence relationship between the components in this embodiment and the components in the present invention will now be clarified. The first substrate layer 1, the second substrate layer 2, the third substrate layer 3, the first solid electrolyte layer 4, the spacer layer 5, and the second solid electrolyte layer 6 according to this embodiment correspond to an element body according to the present invention, the measurement electrode 44 according to this embodiment corresponds to a measurement electrode according to the present invention, the outer pump electrode 23 according to this embodiment corresponds to a measurement-object-gas side electrode according to the present invention, the reference electrode 42 according to this embodiment corresponds to a reference electrode according to the present invention, the reference-gas introduction section 49 corresponds to a reference-gas introduction section, the reference-gas adjustment pump cell 90 according to this embodiment corresponds to a reference-gas adjustment pump cell according to the present invention, the sensor element 101 according to this embodiment corresponds to a sensor element according to the present invention, and the controller 96 according to this embodiment corresponds to a controller according to the present invention. Also, the heater 72 according to this embodiment corresponds to a heater according to the present invention, and the storage unit 98 according to this embodiment corresponds to a storage unit according to the present invention. In this embodiment, an example of a method of diagnosing a moisture absorption state of a gas sensor according to the present invention is also clarified by describing the operation of the control device 95.

According to the gas sensor 100 of this embodiment described above in detail, the control device 95 diagnoses the moisture absorption state around the reference electrode 42 based on the pump current Iph flowing through the reference-gas adjustment pump cell 90 when the reference-gas adjustment pump cell 90 is controlled to pump out the oxygen from the periphery of the reference electrode 42 to the periphery of the outer pump electrode 23. As mentioned above, the pump current Ip3 (=Iph) flowing when the reference-gas adjustment pump cell 90 pumps out the oxygen from the periphery of the reference electrode 42 to the periphery of the outer pump electrode 23 changes depending on the amount of moisture around the reference electrode 42. Accordingly, it is possible to diagnose the moisture absorption state around the reference electrode 42 based on the pump current Iph. Moreover, as the moisture-absorption-state diagnosis process, the control device 95 performs a moisture determination process of determining whether the amount of moisture around the reference electrode 42 is large. The control device 95 performs the moisture-concentration decrease process if it is determined that the amount of moisture is large in the moisture determination process. In this manner, it can be appropriately determined whether to perform the moisture-concentration decrease process based on the diagnostic result of the moisture-absorption-state diagnosis process. Moreover, since the moisture concentration around the reference electrode 42 can be quickly decreased by performing the moisture-concentration decrease process, it is possible to suppress a decrease in the detection accuracy of the specific gas concentration caused by the moisture around the reference electrode 42.

Furthermore, in the moisture-absorption-state diagnosis process, the control device 95 diagnoses the moisture absorption state around the reference electrode 42 based on the pump current Iph when the predetermined control voltage (voltage Vha) higher than the voltages in the limiting current region of the reference-gas adjustment pump cell 90 is applied between the outer pump electrode 23 and the reference electrode 42. When the voltage Vha higher than the voltages in the limiting current region is applied to the reference-gas adjustment pump cell 90, the moisture around the reference electrode 42 is likely to be decomposed. Thus, the amount of moisture around the reference electrode 42 is likely to affect the pump current Iph. Accordingly, by using the pump current Iph when such a voltage Vha is applied, it is possible to more appropriately diagnose the moisture absorption state around the reference electrode 42.

Furthermore, in the moisture-absorption-state diagnosis process, the control device 95 diagnoses the moisture absorption state around the reference electrode 42 based on the comparison between the pump current Iph and the limiting current Iplim of the reference-gas adjustment pump cell 90. When the voltage Vha higher than the voltages in the limiting current region is applied to the reference-gas adjustment pump cell 90, the difference between the pump current Iph and the limiting current Iplim increases as the amount of moisture around the reference electrode 42 increases. Thus, it is possible to more appropriately diagnose the moisture absorption state around the reference electrode 42 by comparing the pump current Iph with the limiting current Iplim.

Furthermore, in the moisture-absorption-state diagnosis process, the control device 95 compares the pump current Iph with the limiting current Iplim stored in the storage unit 98. Accordingly, it is not necessary to measure the limiting current Iplim in the moisture-absorption-state diagnosis process.

Furthermore, when the voltage Vha is a value of 0.8 V or higher, the pump current Iph when a voltage in this range is applied is likely to change depending on the amount of moisture around the reference electrode 42, and thus it is appropriate for performing the moisture-absorption-state diagnosis process. When the voltage Vha is higher than 1.5 V, there is a possibility that oxygen ions in the solid electrolyte of the sensor element 101 become deficient, electron conduction of the solid electrolyte appears, and the sensor element 101 is blackened and cannot be used. However, when the voltage Vha is 1.5 V or lower, blackening of the sensor element 101 can be suppressed.

Furthermore, after electricity is applied to the heater 72 and the temperature of the heater 72 reaches the predetermined temperature or higher, the control device 95 performs the moisture-absorption-state diagnosis process. Accordingly, since the moisture-absorption-state diagnosis process is performed after the temperature of the heater 72 is increased, the reference-gas adjustment pump cell 90 can be operated in a state where the solid electrolyte layer is activated and oxygen ion conductivity is exhibited. Thus, the moisture-absorption-state diagnosis process can be executed at an appropriate timing.

The present invention is not limited to the above-described embodiment, and can be carried out by various modes as long as they belong to the technical scope of the invention.

For example, in the above embodiment, the limiting current Iplim preliminarily stored in the storage unit 98 is used in the moisture-absorption-state diagnosis process, but the configuration is not limited thereto. For example, in the moisture-absorption-state diagnosis process, the control device 95 may apply the voltage Vp3 in the limiting current region to the reference-gas adjustment pump cell 90 and measure the pump current Ip3 flowing at this time as the limiting current Iplim. The value of the voltage Vp3 applied at this time is referred to as a voltage Vhb. The voltage Vhb may be preliminarily determined as a value within the range of the limiting current region (for example, a value within the range between 100 mV and 700 mV inclusive in the example of FIG. 4). Alternatively, in the moisture-absorption-state diagnosis process, the control device 95 may measure the value of the pump current Ip3 while gradually changing the value of the voltage Vhb, and measure, as the limiting current Iplim, the value at the time when it is regarded that the pump current Ip3 no longer changes. In this manner, if not only the pump current Iph but also the limiting current Iplim is measured in the moisture-absorption-state diagnosis process, the determination can be performed with higher accuracy.

In the above embodiment, the moisture absorption state around the reference electrode 42 is diagnosed based on the difference between the pump current Iph and the limiting current Iplim, but the configuration is not limited thereto. The diagnosis may be performed at least by comparing the pump current Iph with the limiting current Iplim. For example, the diagnosis may be performed based on the ratio between the pump current Iph and the limiting current Iplim. The diagnosis may be performed at least based on the pump current Iph, and the limiting current Iplim does not have to be used for the diagnosis. For example, the pump current Iph may be compared with a predetermined threshold, and if the pump current Iph exceeds the threshold, it may be determined that the amount of moisture around the reference electrode 42 is large.

In the above embodiment, after the temperature of the heater 72 reaches the predetermined temperature or higher in step S110, the control device 95 performs the moisture-concentration decrease process, but the configuration is not limited thereto. The moisture-absorption-state diagnosis process may be performed after a predetermined time period elapses since the temperature of the heater 72 has reached the predetermined temperature or higher instead of immediately after the temperature of the heater 72 reaches the predetermined temperature or higher. Alternatively, without performing the determination whether the temperature of the heater 72 has reached the predetermined temperature or higher, the control device 95 may execute the moisture-absorption-state diagnosis process after a predetermined time period elapses since the start of applying electricity to the heater 72.

In the above embodiment, the control device 95 performs the moisture determination process of determining whether the amount of moisture around the reference electrode 42 is large as the moisture-absorption-state diagnosis process, but the configuration is not limited thereto. The control device 95 may at least diagnose the moisture absorption state around the reference electrode 42. For example, the control device 95 may calculate the amount of moisture around the reference electrode 42 based on the pump current Iph as the diagnosis for the moisture absorption state. For example, the relationship between the pump current Iph and the amount of moisture of the reference electrode 42, or the relationship between the difference ΔI and the amount of moisture of the reference electrode 42 may be examined through experiments and stored in the storage unit 98 in advance. The control device 95 may calculate the amount of moisture based on the pump current Iph and the relationship stored in the storage unit 98 in step S130.

In the above embodiment, the control device 95 uses the diagnostic result of the moisture-absorption-state diagnosis process for determining whether to perform the moisture-concentration decrease process, but the configuration is not limited thereto, and the diagnostic result may be used for another purpose. For example, since the potential (reference potential) of the reference electrode 42 changes in accordance with the amount of moisture around the reference electrode 42, the change in the reference potential may be predicted based on the amount of moisture and the control on the pump cells 21, 50, 41, and 90 may be changed. In detail, the control device 95 may calculate the amount of moisture around the reference electrode 42 in the moisture-absorption-state diagnosis process, and at least one of the target values V0*, V1*, and V2* may be changed in accordance with the calculated amount of moisture, or the voltage Vp3 to be applied to the reference-gas adjustment pump cell 90 may be changed in the reference-gas adjustment process.

In the above embodiment, the control device 95 starts the normal-time control process in step S150 after executing the moisture-absorption-state diagnosis process in steps S120 and S130, but the configuration is not limited thereto. The control device 95 may execute the moisture-absorption-state diagnosis process after the normal-time control process is started. For example, the control device 95 may execute the moisture-absorption-state diagnosis process every predetermined time period. In this case, the normal-time control process may be temporarily stopped during execution of the moisture-absorption-state diagnosis process.

In the above embodiment, the voltage Vp3 is a direct-current voltage, but is not limited thereto, and may be a voltage that is repeatedly turned on and off, such as a pulse voltage. Even in this case, the control device 95 can perform the moisture-absorption-state diagnosis process, the moisture-concentration decrease process, and the reference-gas adjustment process. When the voltage Vp3 is a voltage that is repeatedly turned on and off, the control device 95 may measure the voltages V0, V1, and V2 during a period in which the voltage Vp3 is off (in other words, during a period in which the pump current Ip3 does not flow), and use the voltages in the normal-time control process. This makes it possible to perform the moisture-absorption-state diagnosis process and the normal-time control process in parallel without temporarily stopping the normal-time control process during execution of the moisture-absorption-state diagnosis process.

In the above embodiment, the control device 95 may not perform the reference-gas adjustment process.

Figure 7:
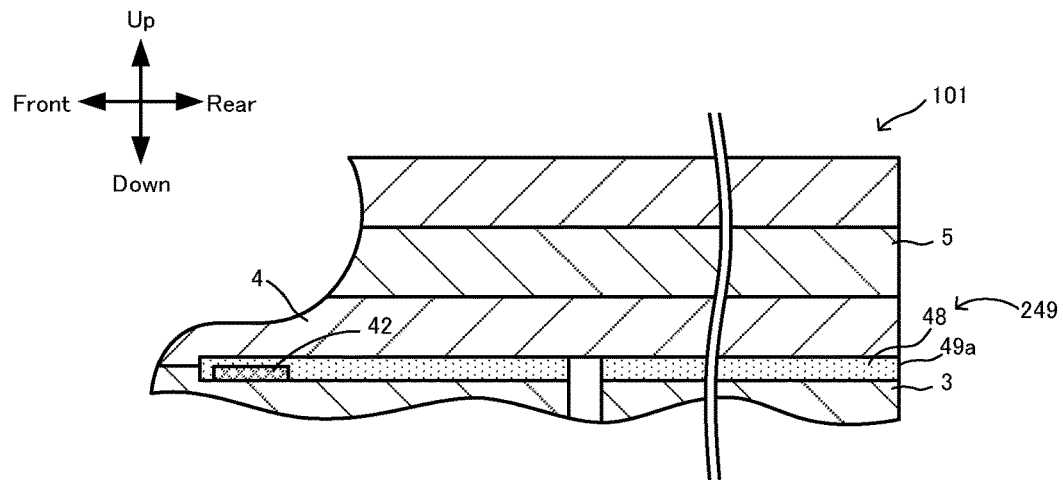
FIG. 7 is a schematic cross-sectional view showing a configuration around a reference-gas introduction section 249 according to a modification.

In the above embodiment, the reference-gas introduction section 49 includes the reference-gas introduction space 43 and the reference-gas introduction layer 48, but may include at least one of the reference-gas introduction space 43 and the reference-gas introduction layer 48. Since the reference-gas introduction layer 48 is likely to adsorb the moisture, in a case where the reference-gas introduction section 49 includes the reference-gas introduction layer 48, it is highly significant to perform the moisture-absorption-state diagnosis process of the present invention. For example, in the above embodiment, a reference-gas introduction section 249 shown in FIG. 7 may be employed instead of the reference-gas introduction section 49. The reference-gas introduction section 249 does not include the reference-gas introduction space 43 but includes a reference-gas introduction layer 48. The reference-gas introduction layer 48 in FIG. 7 is disposed from the periphery of the reference electrode 42 to the rear end surface of the element body of the sensor element 101. A part of the reference-gas introduction layer 48 shown in FIG. 7, which is exposed at the rear end surface of the element body of the sensor element 101, functions as an entrance 49a of the reference-gas introduction section 249. The entrance 49a is exposed to the space 149 outside the sensor element 101.

Figure 8:
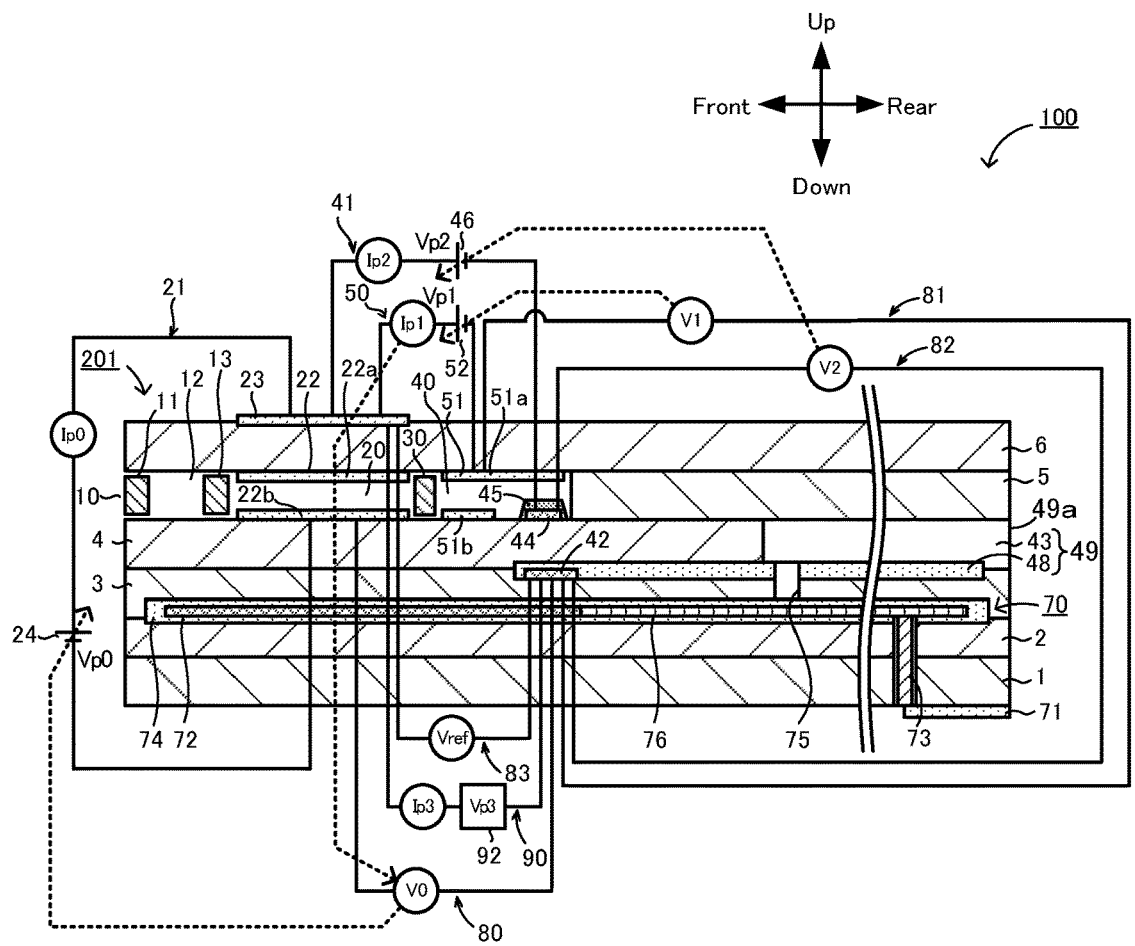
FIG. 8 is a schematic cross-sectional view of a sensor element 201 according to a modification.

In the above embodiment, the sensor element 101 of the gas sensor 100 includes the first internal cavity 20, the second internal cavity 40, and the third internal cavity 61, but the configuration is not limited thereto. For example, the third internal cavity 61 does not have to be provided, as in a sensor element 201 according to a modification shown in FIG. 8. In the sensor element 201 according to the modification shown in FIG. 8, the gas inlet 10, the first diffusion controlling section 11, the buffer space 12, the second diffusion controlling section 13, the first internal cavity 20, the third diffusion controlling section 30, and the second internal cavity 40 are provided next to one another between the lower surface of the second solid electrolyte layer 6 and the upper surface of the first solid electrolyte layer 4 in a communicating manner in that order. Furthermore, the measurement electrode 44 is disposed on the upper surface of the first solid electrolyte layer 4 within the second internal cavity 40. The measurement electrode 44 is covered by a fourth diffusion controlling section 45. The fourth diffusion controlling section 45 is a film formed of a ceramic porous body composed of, for example, alumina ($Al_2O_3$). Similar to the fourth diffusion controlling section 60 according to the above embodiment, the fourth diffusion controlling section 45 has a role of limiting the amount of NOx flowing to the measurement electrode 44. Moreover, the fourth diffusion controlling section 45 also functions as a protective film for the measurement electrode 44. The ceiling electrode 51a of the auxiliary pump electrode 51 is provided to extend to a position directly above the measurement electrode 44. The sensor element 201 having such a configuration is similar to that in the above embodiment in that the measurement pump cell 41 can detect the NOx concentration. In the sensor element 201 in FIG. 8, the periphery of the measurement electrode 44 functions as a measurement chamber. Specifically, the periphery of the measurement electrode 44 has a role similar to that of the third internal cavity 61.

In the above embodiment, the front surface (i.e., the part exposed to the sensor element chamber 133) of the sensor element 101 including the outer pump electrode 23 may be covered with a porous protective layer composed of a ceramic material, such as alumina.

In the above embodiment, the $NO_x$ concentration in the measurement-object gas is detected by the sensor element 101, but is not limited thereto so long as the concentration of a specific gas in the measurement-object gas is detected. For example, instead of $NO_x$, the concentration of another oxide may be detected as the specific gas concentration. If the specific gas is an oxide, oxygen is produced when the specific gas itself is reduced in the third internal cavity 61 similarly to the above embodiment, so that the measurement pump cell 41 can acquire a detection value (e.g., the pump current Ip2) according to this oxygen and detect the specific gas concentration. Furthermore, the specific gas may be a non-oxide, such as ammonia. If the specific gas is a non-oxide, the specific gas is converted into an oxide (e.g., is converted into NO in the case of ammonia), so that oxygen is produced when the converted gas is reduced in the third internal cavity 61. Thus, the measurement pump cell 41 can acquire a detection value (e.g., the pump current Ip2) according to this oxygen and detect the specific gas concentration. For example, the inner pump electrode 22 in the first internal cavity 20 functions as a catalyst, so that the ammonia can be converted into NO in the first internal cavity 20.

In the above embodiment, the element body of the sensor element 101 is a layered body having a plurality of solid electrolyte layers (i.e., layers 1 to 6), but is not limited thereto. The element body of the sensor element 101 may include at least one oxygen-ion-conductive solid electrolyte layer. For example, the layers 1 to 5 other than the second solid electrolyte layer 6 in FIG. 2 may be structural layers (e.g., layers composed of alumina) composed of a material other than that of solid electrolyte layers. In this case, the electrodes in the sensor element 101 may be disposed on the second solid electrolyte layer 6. For example, the measurement electrode 44 in FIG. 2 may be disposed on the lower surface of the second solid electrolyte layer 6. Moreover, the reference-gas introduction space 43 may be provided in the spacer layer 5 instead of the first solid electrolyte layer 4, and the reference-gas introduction layer 48 may be provided between the second solid electrolyte layer 6 and the spacer layer 5 instead of being provided between the first solid electrolyte layer 4 and the third substrate layer 3, and the reference electrode 42 may be provided rearward of the third internal cavity 61 and on the lower surface of the second solid electrolyte layer 6.

In the above embodiment, the outer pump electrode 23 serves as an outer main pump electrode disposed in a part of the main pump cell 21 to be exposed to the measurement-object gas at the outer side of the sensor element 101, an outer auxiliary pump electrode disposed in a part of the auxiliary pump cell 50 to be exposed to the measurement-object gas at the outer side of the sensor element 101, an outer measurement electrode disposed in a part of the measurement pump cell 41 to be exposed to the measurement-object gas at the outer side of the sensor element 101, and a measurement-object-gas side electrode disposed in a part of the reference-gas adjustment pump cell 90 to be exposed to the measurement-object gas at the outer side of the sensor element 101, but is not limited thereto. At least one of the outer main pump electrode, the outer auxiliary pump electrode, the outer measurement electrode, and the measurement-object-gas side electrode may be provided at the outer side of the sensor element 101 in addition to the outer pump electrode 23. The measurement-object-gas side electrode of the reference-gas adjustment pump cell 90 may be provided in the sensor element 101 so that the measurement-object-gas side electrode comes into contact with the measurement-object gas. For example, the measurement-object-gas side electrode may be disposed at the inner side of the sensor element 101 instead of being disposed at the outer side, namely, may be disposed in the measurement-object gas flow section of the sensor element 101. For example, the inner pump electrode 22 may serve as both the electrode (inner main pump electrode) of the main pump cell 21 and the measurement-object-gas side electrode of the reference-gas adjustment pump cell 90, and the reference-gas adjustment pump cell 90 may pump in or pump out the oxygen between the periphery of the inner pump electrode 22 and the periphery of the reference electrode 42.

The inventors of the present invention examined the relationship between the voltage Vhc and the execution period of the moisture-concentration decrease process, and the time period until the reference potential became stable as follows. First, the sensor element 101 and the gas sensor 100 of the above embodiment described with reference to FIGS. 1 to 3 were prepared. The gas sensor 100 was stored in a thermos-hygrostat at a temperature of 40° C. and a humidity of 85% for one week, thereby causing water to be adsorbed in the reference-gas introduction layer 48. Next, the gas sensor 100 was attached to a pipe. A model gas having nitrogen as a base gas and with an oxygen concentration of 0% and NOx concentration of 1500 ppm was prepared, and was caused to flow through the pipe as a measurement-object gas. In this state, the sensor element 101 was driven by the control device 95 to execute the heater control process and the moisture-concentration decrease process. The moisture-concentration decrease process was executed from the timing (time t=0) at which the heater control process was started and the temperature of the heater 72 had reached the predetermined temperature to time t=t1. The moisture-concentration decrease process was performed by controlling the reference-gas adjustment pump cell 90 so as to pump out the oxygen from the periphery of the reference electrode 42. After the end of the moisture-concentration decrease process, the control device 95 executed the normal-time control process to continuously control the pump cells and acquire the voltages V0, V1, and V2, and Vref from the sensor cells. Thereafter, the normal-time control process was continued until 60 minutes had elapsed from the start of driving (start of heating) of the sensor element 101, and the pump current Ip2 during that time period was continuously measured. The value of the pump current Ip2 after a lapse of 60 minutes from the start of the driving of the sensor element 101 was set as a reference value (100%), and a change rate of the value of the pump current Ip2 after a lapse of 10 minutes from the start of the driving of the sensor element 101 with respect to the reference value was calculated. The calculation of the change rate in the above-described procedure was performed by variously changing the voltage Vhc and the execution period of the moisture-concentration decrease process as shown in Table 1, which served as Experimental Examples 1 to 14. The voltage Vhc was variously changed in a range between 0.3 V and 1.5 V inclusive. The execution period (the time period from time t=0 to time t=t1) of the moisture-concentration decrease process was variously changed in a range between 5 seconds and 300 seconds inclusive. The change rate of the pump current Ip2 was calculated similarly to Experimental Examples 1 to 14 except that the normal-time control process was started from time t=0 without executing the moisture-concentration decrease process, which served as Experimental Example 15. In any of Experimental Examples 1 to 15, the reference-gas adjustment pump cell 90 was not operated during the normal-time control process, that is, the reference-gas adjustment process was not performed. In this case, as described above, when moisture is present around the reference electrode 42, the moisture is heated by the heater 72 and turns into a gas, so that the potential of the reference electrode 42 temporarily becomes unstable. This means that, until the potential of the reference electrode 42 becomes stable, the pump current Ip2 is not stable even if the NOx concentration of the measurement-object gas is constant. It is considered that as the change rate of the pump current Ip2 is smaller, the amount of moisture around the reference electrode 42 is smaller at the time point when 10 minutes have elapsed from the start of the driving, and the potential of the reference electrode 42 is more stable. Thus, the length of a stabilization period, which is the time period from the start of the driving of the sensor element 101 until the potential of the reference electrode 42 becomes stable, can be evaluated based on the magnitude of the change rate of the pump current Ip2. A shorter stabilization period is more preferable. Thus, in each of Experimental Examples 1 to 15, when the calculated change rate was 3% or less, the stabilization period was determined to be extremely short ("A"). When the calculated change rate was more than 3% and 5% or less, it was determined that the stabilization period was short ("B"). When the calculated change rate was more than 5%, it was determined that the stabilization period was long ("F"). Table 1 shows the evaluation results of the voltage Vhc, the execution period, and the stabilization period of each of Experimental Examples 1 to 15. As shown in Table 1, it was confirmed that the stabilization period can be shortened in Experimental Examples 1 to 14 in which the moisture-concentration decrease process was executed as compared to Experimental Example 15 in which the moisture-concentration decrease process was not performed. Also, from the results of Experimental Examples 1 to 14, it was confirmed that the stabilization period can be shortened as the voltage Vhc of the moisture-concentration decrease process was larger and the execution period was longer.

TABLE 1

| | Moisture-concentration Decrease Process | | Evaluation Result of |
|---|---|---|---|
| | Voltage Vhc [V] | Execution Period [s] | Stabilization Period |
| Experimental Example 1 | 0.3 | 5 | B |
| Experimental Example 2 | 0.3 | 10 | B |
| Experimental Example 3 | 0.3 | 15 | B |
| Experimental Example 4 | 0.3 | 30 | A |
| Experimental Example 5 | 0.3 | 60 | A |
| Experimental Example 6 | 0.3 | 300 | A |

TABLE 1-continued

|  | Moisture-concentration Decrease Process | | Evaluation Result of |
|---|---|---|---|
|  | Voltage Vhc [V] | Execution Period [s] | Stabilization Period |
| Experimental Example 7 | 0.8 | 5 | B |
| Experimental Example 8 | 0.8 | 10 | A |
| Experimental Example 9 | 0.8 | 30 | A |
| Experimental Example 10 | 0.8 | 60 | A |
| Experimental Example 11 | 1.5 | 5 | A |
| Experimental Example 12 | 1.5 | 10 | A |
| Experimental Example 13 | 1.5 | 30 | A |
| Experimental Example 14 | 1.5 | 60 | A |
| Experimental Example 15 | — | — | F |

The present specification also discloses a technical idea of changing "the gas sensor according to claim 2" in claim 7 at the time of filing of the application to "the gas sensor according to any one of claims 2 to 6", a technical idea of changing "the gas sensor according to claim 1" in claim 8 at the time of filing of the application to "the gas sensor according to any one of claims 1 to 7", and a technical idea of changing "the method of diagnosing the moisture absorption state of the gas sensor according to claim 9" in claim 15 at the time of filing of the application to "the method of diagnosing the moisture absorption state of the gas sensor according to any one of claims 9 to 14".

What is claimed is:

1. A gas sensor that detects a specific gas concentration in a measurement-object gas, the gas sensor comprising:
    a sensor element having
    an element body including an oxygen-ion-conductive solid electrolyte layer and provided with a measurement-object gas flow section therein, the measurement-object gas flow section introducing the measurement-object gas and causing the measurement-object gas to flow therethrough,
    a measurement electrode disposed in the measurement-object gas flow section,
    a measurement-object-gas side electrode provided on the element body so that the measurement-object-gas side electrode comes into contact with the measurement-object gas,
    a reference electrode disposed inside the element body,
    a reference-gas introduction section that causes a reference gas serving as a reference for the detection of the specific gas concentration in the measurement-object gas to flow from outside the element body to the reference electrode, and
    a reference-gas adjustment pump cell constituted by including the measurement-object-gas side electrode and the reference electrode; and
    a controller that performs a moisture-absorption-state diagnosis process of diagnosing a moisture absorption state around the reference electrode based on a pump current flowing through the reference-gas adjustment pump cell when the reference-gas adjustment pump cell is controlled to pump out oxygen from a periphery of the reference electrode to a periphery of the measurement-object-gas side electrode.

2. The gas sensor according to claim 1,
    wherein the controller diagnoses the moisture absorption state around the reference electrode based on the pump current when a predetermined control voltage higher than voltages in a limiting current region of the reference-gas adjustment pump cell is applied between the measurement-object-gas side electrode and the reference electrode in the moisture-absorption-state diagnosis process.

3. The gas sensor according to claim 2,
    wherein the controller diagnoses the moisture absorption state around the reference electrode based on a comparison between the pump current and a limiting current of the reference-gas adjustment pump cell in the moisture-absorption-state diagnosis process.

4. The gas sensor according to claim 3,
    wherein the controller diagnoses the moisture absorption state around the reference electrode based on a difference or a ratio between the pump current and the limiting current in the moisture-absorption-state diagnosis process.

5. The gas sensor according to claim 3,
    wherein the controller includes a storage unit that stores a value of the limiting current, and
    wherein the controller compares the pump current with the limiting current stored in the storage unit in the moisture-absorption-state diagnosis process.

6. The gas sensor according to claim 3,
    wherein the controller compares the pump current with the limiting current measured by applying a voltage in the limiting current region to the reference-gas adjustment pump cell in the moisture-absorption-state diagnosis process.

7. The gas sensor according to claim 2,
    wherein the predetermined control voltage is a voltage between 0.8 V and 1.5 V inclusive.

8. The gas sensor according to claim 1, comprising:
    a heater that heats the element body,
    wherein the controller performs the moisture-absorption-state diagnosis process after electricity is applied to the heater and a temperature of the heater reaches a predetermined temperature or higher.

9. A method of diagnosing a moisture absorption state of a gas sensor that detects a specific gas concentration in a measurement-object gas,
    wherein the gas sensor includes
    a sensor element having
    an element body including an oxygen-ion-conductive solid electrolyte layer and provided with a measurement-object gas flow section therein, the measurement-object gas flow section introducing the measurement-object gas and causing the measurement-object gas to flow therethrough,
    a measurement electrode disposed in the measurement-object gas flow section,
    a measurement-object-gas side electrode provided on the element body so that the measurement-object-gas side electrode comes into contact with the measurement-object gas,
    a reference electrode disposed inside the element body,
    a reference-gas introduction section that causes a reference gas serving as a reference for the detection of the specific gas concentration in the measurement-object gas to flow from outside the element body to the reference electrode, and a reference-gas adjustment pump cell constituted by including the measurement-object-gas side electrode and the reference electrode, the method comprising:

a moisture-absorption-state diagnosis process of diagnosing a moisture absorption state around the reference electrode based on a pump current flowing through the reference-gas adjustment pump cell when the reference-gas adjustment pump cell is controlled to pump out oxygen from a periphery of the reference electrode to a periphery of the measurement-object-gas side electrode.

10. The method of diagnosing the moisture absorption state of the gas sensor according to claim 9, wherein the moisture absorption state around the reference electrode is diagnosed based on the pump current when a predetermined control voltage higher than voltages in a limiting current region of the reference-gas adjustment pump cell is applied between the measurement-object-gas side electrode and the reference electrode in the moisture-absorption-state diagnosis process.

11. The method of diagnosing the moisture absorption state of the gas sensor according to claim 10, wherein the moisture absorption state around the reference electrode is diagnosed based on a comparison between the pump current and a limiting current of the reference-gas adjustment pump cell in the moisture-absorption-state diagnosis process.

12. The method of diagnosing the moisture absorption state of the gas sensor according to claim 11, wherein the moisture absorption state around the reference electrode is diagnosed based on a difference or a ratio between the pump current and the limiting current in the moisture-absorption-state diagnosis process.

13. The method of diagnosing the moisture absorption state of the gas sensor according to claim 11, wherein the gas sensor includes a storage unit that stores a value of the limiting current, and wherein the pump current is compared with the limiting current stored in the storage unit in the moisture-absorption-state diagnosis process.

14. The method of diagnosing the moisture absorption state of the gas sensor according to claim 11, wherein the pump current is compared with the limiting current measured by applying a voltage in the limiting current region to the reference-gas adjustment pump cell in the moisture-absorption-state diagnosis process.

15. The method of diagnosing the moisture absorption state of the gas sensor according to claim 9, wherein the gas sensor includes a heater that heats the element body, and wherein the moisture-absorption-state diagnosis process is performed after electricity is applied to the heater and a temperature of the heater reaches a predetermined temperature or greater.

* * * * *